(12) United States Patent
Calderbank et al.

(10) Patent No.: US 9,780,922 B2
(45) Date of Patent: *Oct. 3, 2017

(54) METHOD AND APPARATUS FOR DATA TRANSMISSION USING MULTIPLE TRANSMIT ANTENNAS

(71) Applicant: AT&T Intellectual Property II, L.P., Atlanta, GA (US)

(72) Inventors: Arthur Robert Calderbank, Durham, NC (US); Ayman F. Naguib, New Providence, NJ (US); Nambirajan Seshadri, Irvine, CA (US); Vahid Tarokh, Cambridge, MA (US)

(73) Assignee: AT&T Intellectual Property II, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/797,647

(22) Filed: Jul. 13, 2015

(65) Prior Publication Data

US 2015/0326352 A1    Nov. 12, 2015

Related U.S. Application Data

(63) Continuation of application No. 14/206,201, filed on Mar. 12, 2014, now Pat. No. 9,083,508, which is a
(Continued)

(51) Int. Cl.
*H04L 1/06* (2006.01)
*H04L 1/00* (2006.01)
(Continued)

(52) U.S. Cl.
CPC ............ *H04L 1/0625* (2013.01); *C07K 14/78* (2013.01); *H04B 7/0669* (2013.01);
(Continued)

(58) Field of Classification Search
CPC ... H04L 5/0023; H04L 1/0625; H04L 1/0003; H04L 27/2602; H04L 1/0009;
(Continued)

(56) References Cited

U.S. PATENT DOCUMENTS 3,633,107 A * 1/1972 Brady .................. H04L 1/06
                                                              375/267
3,781,794 A * 12/1973 Morris .................. H04L 1/08
                                                              375/347

(Continued)

FOREIGN PATENT DOCUMENTS

EP    0607615    12/1993
EP    0854418     1/1998
(Continued)

OTHER PUBLICATIONS

"Integrating Speech Technology with Voice Response Units Systems", IBM Technical Disclosure Bulletin, vol. 38, No. 10, Oct. 1, 1995, pp. 215-216, XP000540471.
(Continued)

*Primary Examiner* — Phung M Chung

(57) ABSTRACT

A method and apparatus for increasing the data rate and providing antenna diversity using multiple transmit antennas utilize a set of bits of a digital signal to generate a codeword. Delay elements may be provided in antenna output channels, or, with suitable code construction, delay may be omitted. n signals represent n symbols of a codeword are transmitted with n different transmit antennas. At the receiver, the noisy received sequence is decoded. The parallel transmission and channel coding enables an increase the data rate over previous techniques, and recovery even under fading conditions. The channel coding may be concatenated with error correction codes under appropriate conditions.

12 Claims, 19 Drawing Sheets

Related U.S. Application Data continuation of application No. 13/776,445, filed on Feb. 25, 2013, now Pat. No. 8,694,876, which is a continuation of application No. 11/974,395, filed on Oct. 12, 2007, now Pat. No. 8,386,898, which is a continuation of application No. 11/115,447, filed on Apr. 27, 2005, now Pat. No. 7,298,794, which is a continuation of application No. 09/545,791, filed on Apr. 7, 2000, now Pat. No. 6,889,355, which is a continuation of application No. 08/847,635, filed on Apr. 25, 1997, now Pat. No. 6,115,427.

(60) Provisional application No. 60/030,571, filed on Nov. 7, 1996, provisional application No. 60/017,046, filed on Apr. 26, 1996.

(51) Int. Cl.

| | |
|---|---|
| *C07K 14/78* | (2006.01) |
| *H04B 7/06* | (2006.01) |
| *H04B 7/08* | (2006.01) |
| *H04L 27/20* | (2006.01) |

(52) U.S. Cl.
CPC ......... *H04B 7/0671* (2013.01); *H04B 7/0891* (2013.01); *H04L 1/0041* (2013.01); *H04L 1/0054* (2013.01); *H04L 1/0057* (2013.01); *H04L 1/0065* (2013.01); *H04L 1/0071* (2013.01); *H04L 1/0618* (2013.01); *H04L 27/20* (2013.01); *A01K 2217/075* (2013.01)

(58) Field of Classification Search
CPC ............... H04L 1/0079; H04L 25/0204; H04L 2025/03414; H04L 2025/03426; H04L 25/03343; H04L 1/04; H04L 27/18; H04L 1/0041; H04L 1/0057; H04L 27/20; H04L 27/32; H04L 1/0042; H04L 27/2601; H04L 1/006; H04L 27/2637; H04L 1/0066; H04L 27/2626; H04B 1/707; H04B 1/708; H04B 7/0669; H04B 7/0671; H04B 1/7183; H04B 7/12; H04B 7/0613

See application file for complete search history.

(56) References Cited

U.S. PATENT DOCUMENTS

| | | | |
|---|---|---|---|
| 4,077,021 A * | 2/1978 | Csajka ................. | H04L 27/186 332/103 |
| 4,457,004 A | 6/1984 | Gersho et al. | |
| 4,483,012 A * | 11/1984 | Wei ..................... | H04L 27/3427 375/244 |
| 4,489,418 A * | 12/1984 | Mazo ................. | H04L 27/3433 375/246 |
| 4,520,490 A * | 5/1985 | Wei ...................... | H04L 1/0054 375/246 |
| 4,597,090 A | 6/1986 | Forney, Jr. | |
| 4,945,549 A | 7/1990 | Simon et al. | |
| 5,029,185 A | 7/1991 | Wei | |
| 5,208,816 A | 5/1993 | Seshardi et al. | |
| 5,231,691 A | 7/1993 | Yasuda | |
| 5,303,353 A | 4/1994 | Matsuura et al. | |
| 5,305,352 A * | 4/1994 | Calderbank ........... | H03M 13/35 375/261 |
| 5,305,353 A * | 4/1994 | Weerackody ............ | H04L 1/06 375/260 |
| 5,396,518 A | 3/1995 | How | |
| 5,406,585 A | 4/1995 | Rohani et al. | |
| 5,418,798 A | 5/1995 | Wei | |
| 5,425,128 A | 6/1995 | Morrison | |
| 5,457,478 A | 10/1995 | Frank | |
| 5,475,792 A | 12/1995 | Stanford et al. | |
| 5,479,448 A * | 12/1995 | Seshadri .............. | H04B 7/0604 375/260 |
| 5,513,298 A | 4/1996 | Stanford et al. | |
| 5,524,169 A | 6/1996 | Cohen et al. | |
| 5,548,729 A | 8/1996 | Akiyoshi et al. | |
| 5,553,119 A | 9/1996 | McAllister et al. | |
| 5,623,605 A | 4/1997 | Keshav et al. | |
| 5,659,578 A | 8/1997 | Alamouti et al. | |
| 5,682,478 A | 10/1997 | Watson et al. | |
| 5,732,219 A | 3/1998 | Blumer et al. | |
| 5,737,365 A | 4/1998 | Gilbert et al. | |
| 5,745,754 A | 4/1998 | Lagarde et al. | |
| 5,745,874 A | 4/1998 | Neely | |
| 5,752,232 A | 5/1998 | Basore et al. | |
| 5,796,788 A | 8/1998 | Bottomley | |
| 5,844,951 A | 12/1998 | Proakis et al. | |
| 5,867,478 A | 2/1999 | Baum et al. | |
| 5,884,192 A * | 3/1999 | Karlsson .................. | H01Q 3/26 375/229 |
| 5,890,123 A | 3/1999 | Brown et al. | |
| 5,915,001 A | 6/1999 | Uppaluru | |
| 5,931,965 A | 8/1999 | Alamouti | |
| 5,949,796 A | 9/1999 | Kumar | |
| 6,078,886 A | 6/2000 | Dragosh et al. | |
| 6,115,427 A | 9/2000 | Calderbank et al. | |
| 6,366,886 B1 | 4/2002 | Dragosh et al. | |
| 6,578,173 B2 | 6/2003 | Alamouti | |
| 6,604,077 B2 | 8/2003 | Dragosh et al. | |
| 6,889,355 B1 | 5/2005 | Calderbank et al. | |
| 6,889,356 B1 | 5/2005 | Alamouti | |
| 7,065,148 B2 | 6/2006 | Seshadri et al. | |
| 7,298,794 B2 | 11/2007 | Calderbank et al. | |
| 7,409,013 B2 | 8/2008 | Seshadri et al. | |
| 8,037,396 B2 | 10/2011 | Alamouti | |
| 8,386,898 B2 | 2/2013 | Calderbank et al. | |

FOREIGN PATENT DOCUMENTS

| | | |
|---|---|---|
| GB | 2183880 | 6/1987 |
| JP | 58-015341 | 1/1983 |
| JP | 06-021856 | 1/1994 |
| JP | 06-037683 | 2/1994 |
| JP | H07222248 | 8/1995 |
| WO | WO 99/14871 | 3/1999 |

OTHER PUBLICATIONS

Calson, S. et al., "Application of Speech Recognition Technology to ITS Advanced Traveler Information Systems". Pacific Rim Transtech Conference Vehicle Navigation and Information Systems Conference Proceedings, Washington, Jul. 30-Aug. 2, 1995, No. CONF 6. Jul. 30, 1995, pp. 118-125, XP000641143, IEEE. paragraph II.

"Client-Server Model for Speech Recognition", IBM Technical Disclosure Bulletin, vol. 36, No. 3, Mar. 1, 1993. pp. 25-26, XP000354688.

Saadawi et al., "Fundamentals of Telecommunication Networks", Sep. 15, 1994, A Wiley-Interscience Publication. pp. 23, 33, 279, 317-319.

Tarokh et al., "Space-Time Codes for High Data Rate Wireless Communication: Performance Criteria in the Presence of Channel Estimation Errors, Mobility, and Multiple Paths", IEEE Trans. on Communications, vol. 47, No. 2, Feb. 1999.

J. Wu et al., "Multilevel Trellis MPSK Modulation Codes for the Rayleigh Fading Channel", IEEE Trans. on Communications, vol. 41, No. 9, Sep. 1993.

Wittenben, "Base Station Modulation Diversity for Digital SIMULCASE", 41$^{st}$ IEEE Vehicular Technology Society Conference Proceedings, pp. 848-853, 2000.

Examiner's Office Letter. Japanese Patent Application No. H9-539075, Nov. 7, 2006, pp. 1-3.

European Search Report for EP 97921395. Jan. 15, 1999, copy consists of 3 unnumbered pages.

International Search Report for PCT/US97/07010, Aug. 28, 1997, copy consists of 3 unnumbered pages.

(56) References Cited

OTHER PUBLICATIONS

PCT Written Opinion for PCT/US97/07010, Jan. 15, 1999, copy consists of 7 unnumbered pages.
European Search Report for EP 10183066, Nov. 4, 2011, copy consists of 4 unnumbered pages.
Russell, M. et al., "Interchannel Intereference Analysis of OFDM in a Mobile Environment", Vehicular Technology Conference, Jul. 25-28, 1995, IEEE. vol. 2, pp. 820-824.
Wen-Yi Kuo et al., "Design and Analysis of Transmitter Diversity Using Intentional Frequency Offset", Military Communications Conference, San Diego, CA, Nov. 5-8, 1995, vol. 2, pp. 529-533.
Extended European Search Report for EP Patent Application No. 10154911.1, Nov. 21, 2011.
Pietrobon et al., "Trellis-Coded Multidimensional Phase Modulation", IEEE Transactions on Information, vol. 36, No. 1, Jan. 1990.

\* cited by examiner 01 02 03 04 STATE 0
10 11 12 13 STATE 1
20 21 22 23 STATE 2
30 31 32 33 STATE 3

00, 01, 02, 03, 04, 05, 06, 07,
50, 51, 52, 53, 54, 55, 56, 57,
20, 21, 22, 23, 24, 25, 26, 27,
70, 71, 72, 73, 74, 75, 76, 77,
40, 41, 42, 43, 44, 45, 46, 47,
10, 11, 12, 13, 14, 15, 16, 17,
60, 61, 62, 63, 64, 65, 66, 67,
30, 31, 32, 33, 34, 35, 36, 37, 00, 01, 02, 03,
10, 11, 12, 13,
20, 21, 22, 23,
30, 31, 32, 33,
22, 23, 20, 21,
32, 33, 30, 31,
02, 03, 00, 01,
12, 13, 10, 11, 00, 01, 02, 03,
12, 13, 10, 11,
20, 21, 22, 23,
32, 33, 30, 31,
20, 21, 22, 23,
32, 33, 30, 31,
00, 01, 02, 03,
12, 13, 10, 11,
02, 03, 00, 01,
10, 11, 12, 13,
22, 23, 20, 21,
30 31 32 33
22, 23, 20, 21,
30, 31, 32, 33,
02, 03, 00, 01,
10, 11, 12, 13, 00, 01, 02,0 03, 04, 05, 06, 07, 08, 09, 010, 011, 012, 013, 014, 015
110, 111, 112, 113, 114, 115, 116, 117, 118, 119, 1110, 1111, 1112, 1113, 1114, 1115
20, 21, 22, ,23, 24, 25, 26, 27, 28, 29, 210, 211, 212, 213, 214, 215
90, 91, 92, 93, 94, 95, 96, 97, 98, 99, 910, 911, 912, 913, 914, 915
40, 41, 42, 43, 44, 45, 46, 47, 48, 49,410, 411, 412, 413, 414, 415
150, 151, 152, 153, 154, 155, 156, 157, 158, 159, 1510, 1511, 1512, 1513, 1514, 1515
60, 61, 62, 63, 64, 65, 66, 67, 68, 69, 610, 611, 612, 613, 614, 615
130, 131, 132, 133, 134, 135, 136, 137, 138, 139, 1310, 1311, 1312, 1313, 1314, 1315
80, 81, 82, 83, 84, 85, 86, 87, 88, 89, 8010, 8011, 8012, 8013, 8014, 8015
30, 31, 32, 33, 34, 35, 36, 37, 38, 39, 3010, 3011, 3012, 3013, 3014, 3015
100, 101, 102, 103, 104, 105, 106, 107, 108, 109, 1010, 1011, 1012, 1013, 1014, 1015
10, 11, 12, 13, 14, 15, 16, 17, 18, 19, 1010, 1011, 1012, 1013, 1014, 1015
120, 121, 122, 123, 124, 125, 126, 127, 128, 129, 1210, 1211, 1212, 1213, 1214, 1215
70, 71, 72, 73, 74, 75, 76, 77, 78, 79, 7010, 7011, 7012, 7013, 7014, 7015
140, 141, 142, 143, 144, 145, 146, 147, 148, 149, 1410, 1411, 1412, 1413, 1414, 1415
50, 51, 52, 53, 54, 55, 56, 57, 58, 59, 5010, 5011, 5012, 5013, 5014, 5015

00, 01, 02, ... ,015
10, 11, 12, ... ,115
20, 21, 22, ... ,215
30, 31, 32, ... ,315
40, 41, 42, ... ,415
50, 51, 52, ... ,515
60, 61, 62, ... ,615
70, 71, 72, ... ,715
80, 81, 82, ... ,815
90, 91, 92, ... ,915
100, 101, ... ,1015
110, 111, ... ,1115
120, 121, ... ,1215
130, 131, ... ,1315
140, 141, ... ,1415
150, 151, ... ,1515

METHOD AND APPARATUS FOR DATA TRANSMISSION USING MULTIPLE TRANSMIT ANTENNAS

This application is a continuation of U.S. patent application Ser. No. 14/206,201, filed Mar. 12, 2014, now U.S. Pat. No. 9,083,508, issued on Jul. 14, 2015, which is a continuation of U.S. patent application Ser. No. 13/776,445, filed Feb. 25, 2013, now U.S. Pat. No. 8,694,876, filed Apr. 8, 2014, which is a continuation of U.S. patent application Ser. No. 11/974,395, filed Oct. 12, 2007, now U.S. Pat. No. 8,386,898, issued Feb. 26, 2013; which is a continuation of U.S. patent application Ser. No. 11/115,447, filed Apr. 27, 2005, now U.S. Pat. No. 7,298,794, issued Nov. 20, 2007; which is a continuation of U.S. patent application Ser. No. 09/545,791, filed Apr. 7, 2000, now U.S. Pat. No. 6,889,355, issued May 3, 2005; which is a continuation of U.S. patent application Ser. No. 08/847,635 filed Apr. 25, 1997, now U.S. Pat. No. 6,115,427, issued Apr. 25, 1997; which claims priority to U.S. Provisional Application No. 60/017,046 filed Apr. 26, 1996 and to U.S. Provisional Application No. 60/030,571 filed Nov. 7, 1996, all of which are herein incorporated by reference in their entirety.

BACKGROUND OF THE INVENTION

1. Field of Invention

The present invention relates generally to the field of communications systems, and particularly to the field of wireless communications, such as cellular radio.

2. Description of Related Art

Antenna diversity is a technique used in communication system, including mobile cellular radio, to reduce the effects of multi-path distortion fading. Antenna diversity may be obtained by providing a receiver with two or more (n≥2) antennas. These n antennas, when, properly positioned, imply n channels which suffer fading in different manners. When one channel is in deep fade—that is, suffering severe amplitude and phase loss due to the destructive effects of multi-path interference, another of these channels is unlikely to be suffering from the same effect simultaneously. The redundancy provided by these independent channels enables a receiver to often avoid the detrimental effects of fading.

Alternatively, antenna diversity benefit can be provided to a mobile receiver by providing multiple transmitting antennas at a base or transmitting station, rather than at the receiver. The receiver can therefore use a single antenna, saving cost and complexity at that side of the transmission chain.

Multiple transmit antennas can be provided at the base station in a variety of way. A schematic diagram of certain possible known techniques is illustrated in FIG. 1. Perhaps most simply, as schematically illustrated in FIG. 1(a) two antennas can be provided at the output stage, and the information signal $d_k$ can be switched between two matched antenna elements, without overlap in time or frequency. Of course this has the drawback that the transmitter requires feedback from the receiver about the channels corresponding to each transmit antenna. This scheme does not perform well when the channel is rapidly changing.

In a variant described in U.S. Pat. No. 5,479,448 and schematically illustrated in FIG. 1(b), the above mentioned drawbacks of switch diversity are removed by using a channel code to provide diversity benefit. Maximum diversity is upper-bounded by the number of antenna elements at the base station, and is equal to the minimum Hamming distance of the channel code used, provided that the receiver is equipped with one antenna. The system described in that patent is applicable to both FDD (frequency division duplex) and TDD (time division duplex)-based systems.

Illustrative embodiments of the system of U.S. Pat. No. 5,479,448 comprise a base station which employs a channel code of length n≥2 symbols (n being the number of antennas used by the transmitter), and a minimum Hamming distance $2 \geq d_{min} \geq n$. This channel code is used to encode a group of k information bits. The n antennas of the base station transmitter are separated by a few wavelengths, as is conventional to provide the diversity reception with the n antennas. The channel code symbol $c_i$ is transmitted with the $i^{th}$ antenna to represent these k bits. At a receiver, a conventional maximum likelihood channel code decoder provides a diversity advantage of $d_{min}$.

In the preferred embodiment of U.S. Pat. No. 5,479,448, the transmitted signals from different antennas are separated in time. This results in data rate reduction, sacrificing bandwidth. The reduction in data rate is equal to the number of antennas (or length of the code).

Transmit bandwidth can be improved over the diversity arrangement of FIG. 1(b), by splitting the information signal into two paths to the two antennas, the second of which has a delay element or tap as disclosed in A. Wittneben, "Base Station Modulation Diversity for Digital SIMULCAST," $41^{st}$ IEEE Vehicular Technology Society Conference Proceedings, pp. 848-853 and shown in FIG. 1(c). The signal appearing at B at any given instant of time is therefore the same signal as appeared at antenna A the preceding instant of time. The two signals are transmitted simultaneously, reconstructed at the receiving station, and processed to isolate the desired information signal.

SUMMARY OF THE INVENTION

The invention improving on these and other communication techniques in one aspect relates to a system and method for data transmission using multiple transmit antennas.

The invention in one aspect relates to the system and method for data transmission which increases effective utilization of available channel bandwidth, without great increases in transmitter or receiver complexity or cost. The invention in another aspect relates to a system and method for data transmission which utilizes channel-codes to transmit data, reducing the chance of error and increasing reception robustness.

The invention in another aspect relates to a system and method for data transmission which can include concatenated error correcting codes, even further increasing BER and other transmission performance.

The invention in another aspect relates to a system and method for data transmission which can include multilevel coding, and decreases decoding complexity.

The invention in another aspect relates to a system and method for data transmission which preserves diversity benefit from multiple antenna arrangements, under a wide range of conditions.

In the present invention, among other advantages the time separation described in U.S. Pat. No. 5,749,448 is removed, and coded data is transmitted in parallel, simultaneously from different transmit antennas, with or without delay. Increased data rate as well as diversity are achieved.

By way of comparison, the codes described in U.S. Pat. No. 5,749,448 (col. 6, lines 21-29; col. 7, lines 35-44 and 63-67; col. 8, lines 1-16) provide a diversity 2 using 2 transmit antennas and 1 receive antenna. The bandwidth efficiencies for these disclosed codes are 1 bit/symbol, 1.5 bits/symbol and 2 bits/symbol respectively.

Using the present invention as described below, applying the same codes but a new transmission arrangement, the bandwidth efficiency doubles to 2, 3 and 4 bits/symbol respectively. Moreover, in another embodiment of the present invention when coding is done taking into account diversity and other criteria, no delay element on the antenna line is necessary to implement the invention and further coding gain is obtained.

DETAILED DESCRIPTION OF PREFERRED EMBODIMENTS

A. Incorporation by Reference

Various concepts of digital signal processing referred to in this application are well known in, for example, the digital communication and other arts, and thus they need not be described in detail herein. These concepts are described for instance in U.S. Pat. No. 4,457,004, issued Jun. 26, 1984 to A. Gersho et al.; U.S. Pat. No. 4,489,418, issued Dec. 18, 2984 to J. E. Mazo; U.S. Pat. No. 4,520,490, issued May 28, 1985 to L. Wei; U.S. Pat. No. 4,597,090, issued Jun. 24, 1986 to G. D. Forney, Jr.; U.S. Pat. No. 5,029,185 issued Jul. 2, 1991 to L. Wei; in A. Wittneben, "Base Station Modulation Diversity for Digital SIMULCAST," 41$^{st}$. IEEE Vehicular Technology Society Conference Proceedings, pp. 848-853; and U.S. Pat. No. 5,479,448 to Seshadri, all of which are incorporated by reference.

B. Illustrative Hardware Used in Embodiments

For clarity of explanation, illustrative embodiments of the present invention are presented as comprising individual functional blocks. As known in the art, the functions these blocks represent may be provided through the use of either shared or dedicated hardware (processors), including, but not limited to, hardware capable of executing software. The software is stored on a computer-readable storage device such that the functions as instructed by the software can be performed by the processor. Illustrative embodiments may comprise digital signal processor (DSP) hardware, and software performing the operations discussed below. Very large scale integration (VLSI) hardware embodiments of the present invention, as well as hybrid DSP/VLSI embodiments, may also be constructed.

C. Introduction to Illustrative Embodiments

The central idea of conventional antenna diversity reception is that with high probability, a signal received at different antennas undergoes fading at different moments in time. Thus, a receiver can combine or select different receive signals to reconstruct the transmitted signal with little distortion.

Figure 1A:
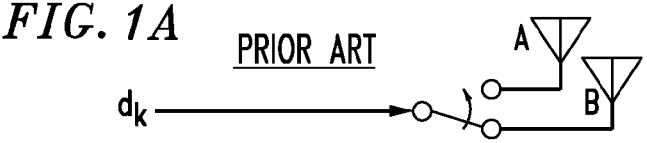
FIGS. 1(a), 1(b) and 1(c) illustrate a schematic diagram of certain prior approaches to multiple transmit antennas at base stations.
Figure 1B:
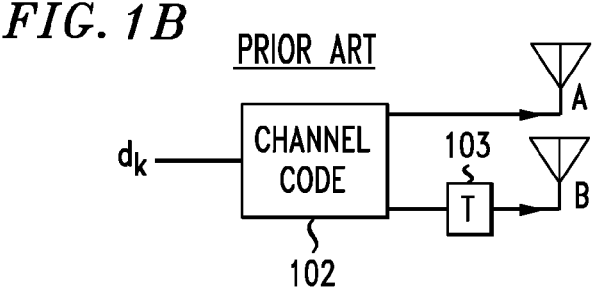
Figure 1C:
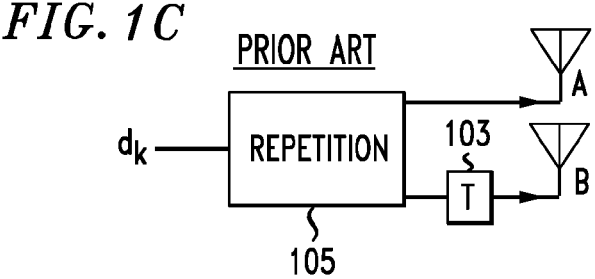
Figure 2A:
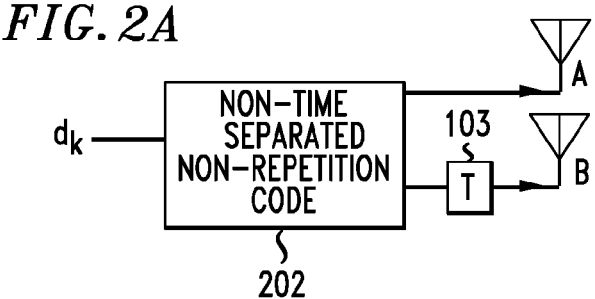
FIGS. 2(a) and 2(b) illustrate a schematic block diagram of first and second embodiments of multiple transmit antenna base stations, according to the invention.
Figure 2B:
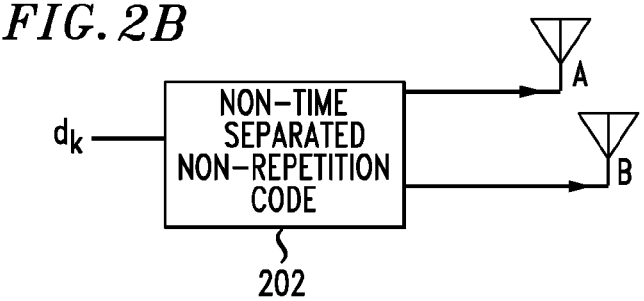

The present invention provides the benefit of diversity by taking advantage of multiple antennas at a transmitter, with or without delay. A first illustrative embodiment shown in FIGS. 2(a) and 3 maps the information sequence of length $M_1$ to a two code sequence of length $M_2$. In particular every group of k input bits (assume k divides $M_1$) are mapped to first and second code symbols. The two code symbols are used to form two code sequences where each sequence is of length $M_1/k=M_2$ where the first code sequence is comprised of the first code sequence is comprised of the second code symbol. These two code sequences are then used to phase modulate a carrier using conventional phase shift keying, as is well known in the art, and in that process two modulated signals are generated. Alternatively, quadrature amplitude modulation, or any other modulation scheme can be used.

The two modulated signals are then transmitted using two transmit antennas. In the first illustrative embodiment, a timing offset of one symbol interval (delay element or tap, of period T) is introduced between the two signals. The receiver receives a sum of faded versions of the transmitted signals from the two antennas, perturbed by noise. In the second illustrative embodiment, the use of a delay in one of the antenna channels is eliminated.

Because the two coded signals are transmitted simultaneously, no bandwidth penalty is incurred. However intersymbol interference is created which is resolved at the receiver using maximum likelihood sequence detection or other techniques that are known in the art. As noted, the introduction of delay to provide diversity is known in the art. However the use of coding as an integral part of the delay diversity arrangement is not known, nor is elimination of any delay element using codes which adhere to diversity and other criteria. Prior to proceeding with a description of the illustrative embodiments of the present invention, concepts related to a channel model for the first illustrative embodiment and embodiment error performance will be presented.

D. Channel Model Transmission Format: Analysis in First Illustrative Embodiment The overall transmission environment in which the first illustrative embodiment of the invention operates may be viewed as comprising n distinct channels, each illustratively undergoing independent slow (static) Rayleigh fading (it should be understood that the principles of the present invention are applicable to other classes of fading channels as well). The impulse response for the $i^{th}$ channel is given by $$h_1(t)=\alpha_1\delta(t)e^{j\omega_0 t}, 1\leq i\leq N \quad (1)$$

where $\omega_0$ is the angular carrier frequency and $z_i$ is the static complex fade value whose phase is a random variable that is uniformly distributed over $[-\pi, \pi)$, and whose magnitude is Rayleigh distributed with $$P(|\alpha_1|e^{-|\alpha_1|^2}, z_1 \geq 0 \quad (2)$$

Figure 4:
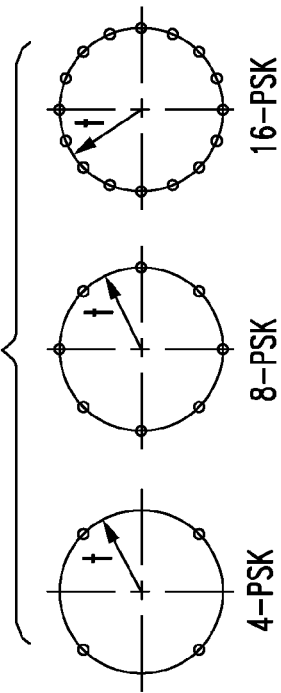
FIG. 4 illustrates signal constellations used in implementations of the invention.

The information sequence I is grouped into sub-sequences of k information bits, $$I = \Big(\underbrace{I_0^1, I_1^1, I_2^1, \ldots, I_{k-1}^1}_{\text{1st sub-sequence}}, \underbrace{I_0^2, \ldots, I_{k-1}^2}_{\text{2nd sub-sequence}}, \ldots\Big).$$

where the superscript is the sub-sequence number. Each sub-sequence is mapped into n channel symbols of the channel constellation using a cannel code. Some of the illustrative signal constellations are shown in FIG. 4. The signal constellation mapped code sequence is $$c = \Big(\underbrace{c_0^1, \ldots, c_{n-1}^1}_{\substack{\text{code sequence for}\\ \text{1st sub-sequence}}}, \underbrace{c_0^2, \ldots, c_{n-1}^2}_{\substack{\text{code sequence for}\\ \text{2nd sub-sequence}}}, \ldots\Big).$$

Hence each element $c_i^j$ is a point belonging to a signal constellation. The code sequence is arranged in a matrix as shown below $$\begin{bmatrix} c_0^1 & c_0^2 & c_0^3 & \ldots \\ c_1^1 & c_1^2 & c_1^3 & \\ \vdots & & & \\ c_{n-1}^1 & c_{n-1}^2 & c_{n-1}^3 & \ldots \end{bmatrix}.$$

The first row of the matrix is pulse shaped using square-root Nyquist filter (p(t), modulated and transmitted using antenna 1. The second row of the matrix is pulse shaped using square-root Nyquist filter p(t−T) (p(t) delayed by one symbol interval). The $i^{th}$ row of the matrix is transmitted using square root Nyquist filter p(t−(i−1)T) (p(t) delayed by (i−1) symbol intervals). At the receiver, the received signal, following demodulation, receiver filtering and sampling as is well known in the art, is given by $$r_i=\alpha_0 c_0^i+\alpha_1 c_1^{i-1}+\alpha_2^{i-2}+\ldots+\alpha_{n-j}c_{n-j}^{i-(n-1)}+\eta_i$$

where $\eta_i$ is the extraneous noise which is modeled as addictive white Gaussian.

Decoding is done in a conventional manner using maximum likelihood decoding techniques or suboptimum variants thereof, which are well known in the art.

E. First Illustrative Embodiment

Figure 3:
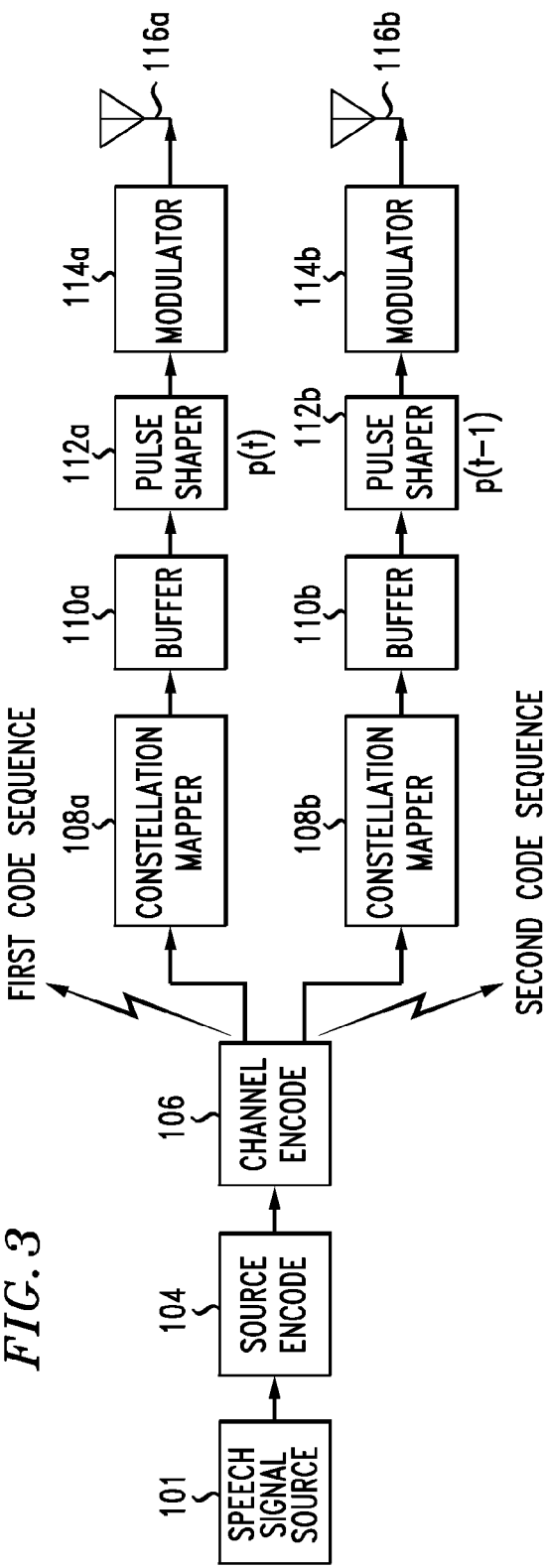
FIG. 3 illustrates a schematic block diagram of a wireless communication system constructed according to the illustrative first embodiment of the invention.

FIG. 3 presents an illustrative apparatus of a digital wireless communication system transmitter according to a first illustrative embodiment of the present invention. The transmitter receives an analog speech signal from speech signal source 101, and processes this signal for transmission on antennas 116a, b. The transmitter comprises a source encoder 104, a channel encoder 106, constellation mappers 108a, b, temporary storage buffers 110a, b, pulse shapers 112a and b, the modulators 114a, b. Power amplification associated with the transmission of radio signals has been omitted from FIG. 3 for clarity.

The speech signal source 101 provides an analog speech signal to be encoded and transmitted for instance to a mobile receiver. This speech signal is converted to a digital signal by conventional analog-to-digital conversion by source encoder 104. Source encoder 104 provides a digital signal representative of the analog speech signal as output to channel encoder 106. Source encoder 104 may be realized with any of the conventional speech encoders.

The channel encoder 106 receives the PCM (Pulse Code Modulated) digital signal comprising a plurality of bits from the source encoder 104. Channel encoder 106 codes the PCM digital signal using a conventional channel code. Any channel code may be employed for this purpose, as long as it is appropriately constructed.

The code constructed for the first illustrative embodiment of the present invention assumes that the number of antennas at the base station is two. The following illustrative code of length n=2 complex symbols (2 symbols×2 components (in-phase and quadrature) per symbol equals 4 dimensions (4-D)), has a minimum Hamming distance $d_{min}$=2.

| Channel Code | | |
|---|---|---|
| Information Bits | Symbol 1 | Symbol 2 |
| 00 | 0 | 0 |
| 01 | 1 | 2 |
| 11 | 2 | 1 |
| 10 | 3 | 3 |

Using this code, encoder 106 codes two information bits at a time to generate one of four codewords. Each generated codeword comprises two symbols (see columns labeled Symbol 1 and Symbol 2, above). Each symbol belongs to the 4-PSK constellation presented in FIG. 4(*a*). Thus, a coding rate of one information bit per code symbol is provided by this code. Symbol 1 is transmitted with antenna 116*a* and symbol 2 with antenna 116*b*, as discussed below.

The first symbol of each codeword generated by encoder 106 is provided as input to constellation mapper 108*a*, and the second symbol of the codeword is provided to mapper 108*b*.

Constellation mappers 108*a, b* produce a complex valued output corresponding to a symbol received from encoder 106. The real part of this output determines an in-phase component of a modulated signal transmitted at antennas 116*a,b*. Similarly, the imaginary part of the output determines a quadrature component of the modulated signal. The constellation mapper 108*a,b* are conventional mappers known in the art. They may be realized as a look-up table or as a straightforward combination of logic elements. Mappers 108*a,b* operate on the first and second symbol of each received codeword, respectively, and provide complex valued output to buffers 110*a* and *b*.

Buffers 110*a* and *b* provide temporary storage for the complex values received form mappers 108*a, b*, and illustratively store 100 of such values. The complex entries in buffer 110*a* are pulse shaped using conventional square-root Nyquist transmit filter (see 112*a*) while those in buffer 110*b* are pulse shaped using the same square-r00t Nyquist transmit filter but whose impulse response is delayed by one symbol interval (see 112*b*). The pulse shaped outputs are then modulated by modulators 114*a* and 114*b* and transmitted using antennas 116*a* and 116*b*. Additional filtering and power amplification stages are not shown for clarity.

F. Further Channel Codes for First Illustrative Embodiment

The first embodiment described above may employ other channel codes than the one first developed, to enhance coding efficiency. For example, the following code length 2, $d_{min}$=2, is formed from an 8-PSK constellation shown in FIG. 4(*b*). This code has efficiency of 3 bits/symbol:

| Information Data | Symbol 1 | Symbol 2 |
|---|---|---|
| 000 | 0 | 0 |
| 001 | 1 | 5 |
| 011 | 2 | 2 |
| 111 | 3 | 7 |
| 100 | 4 | 4 |
| 101 | 5 | 1 |
| 110 | 6 | 6 |
| 111 | 7 | 3 |

A distinct pair of codewords differ in at least two positions.

In another coding implementation, a coding efficiency of 4.0 bits/symbol is provided. In order to achieve $d_{min}$=2 and stay within the constraint that the block length of the code equal two, it is necessary to have at least 16 codewords. Hence, 16-PSK (see FIG. 4(*c*)) is the smallest constellation with which a diversity benefit of 2 can be provided. The 4D-16 PSK code is shown below:

| Information Data | Symbol 1 | Symbol 2 |
|---|---|---|
| 0000 | 0 | 0 |
| 0001 | 2 | 2 |
| 0010 | 4 | 4 |
| 0011 | 6 | 6 |
| 0100 | 8 | 8 |
| 0101 | 10 | 10 |
| 0110 | 12 | 12 |
| 0111 | 14 | 14 |
| 1000 | 1 | 7 |
| 1001 | 3 | 9 |
| 1010 | 5 | 11 |
| 1011 | 7 | 13 |
| 1100 | 9 | 15 |
| 1101 | 11 | 1 |
| 1110 | 13 | 3 |
| 1111 | 15 | 5 |

G. An Illustrative Decoder for Embodiments

Figure 5:
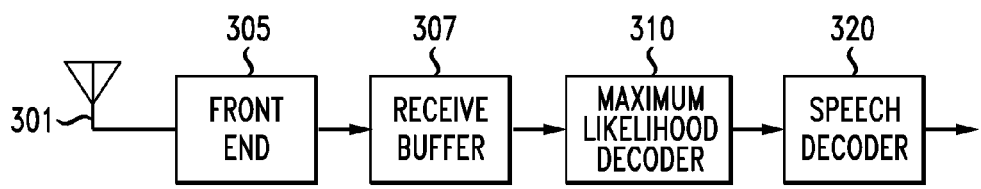
FIG. 5 illustrates a schematic block diagram of a receiver constructed in conjunction with the first illustrative embodiment of the invention.

FIG. 5 presents an illustrative receiver 300 according to the foregoing first illustrative embodiment of the present invention. Receiver 300 receives transmitted signals from antenna 301, and produces analog speech as output. Receiver 300 comprises an RF-to-baseband from end 305, receive buffer 307, channel decoder 310, and speech decoder 320.

The RF-to-baseband front end 305 provides conventional demodulated output (e.g., received symbols) to the receive buffers 307. Front end 305 includes, e.g., conventional RF to IF conversion, receive filtering, and tinting and carrier recovery circuits.

Receive buffer 307 store received symbols from front end 305. Buffer 307 analogous to buffers 110*a, b* of the illustrative transmitter described in Section D and present in FIG. 3 except that since the receiver receives a superposition of data in buffers 110*a, b* only one buffer is needed. Channel decoder 210 receives the demodulated symbol output from buffer 307, and provides decoded information bits to speech decoder 320. The illustrative decoder 310 operates in accordance with the flow diagram presented in FIG. 6.

Figure 6:
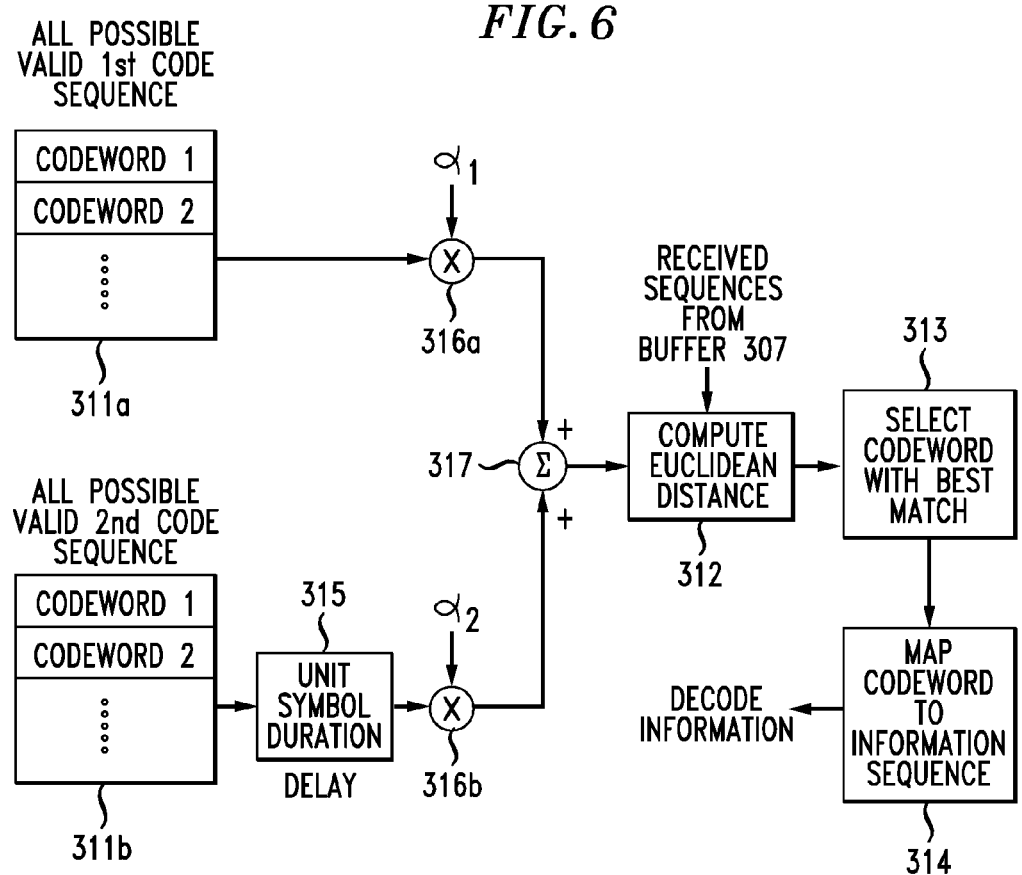
FIG. 6 illustrates a schematic block diagram of decoding circuitry used in the receiver constructed according to the first illustrative embodiment of the invention.

As shown in FIG. 6, symbols from receive buffer 307 are used in computing distances with all possible valid codewords stored in memories 311*a, b*. For example the first codeword from buffer 311*a* taken together with the first codeword from 311*b*, but delayed by one unit symbol interval are linearly combined with channel gains $\alpha_1$ and $\alpha_2$ respectively. The distance between this combined output and the received symbols in buffer 307 is computed. This is done for every codeword in buffers 311a and 311b (see 312). The legal codeword pair is the one which most closely match the received sequence (see 313). The decoded codeword pair is then mapped to a string of bits which comprises coded information (see 314). This exhaustive search can be implemented efficiently using the Viterbi algorithm or variants thereof, known to persons skilled in the art.

Speech decoder 320 is a conventional device providing a mapping of digital speech information to analog speech. Decoder 320 provides an inverse operation to source encoder 104 discussed above with respect to FIG. 5.

In light of the discussion above, it is to be understood that the diversity benefit of the present invention using one antenna may be enhanced by use of multiple receive antennas. This advantage may be realized by combination of a front end and receive buffer for each receiver antenna.

Figure 7:
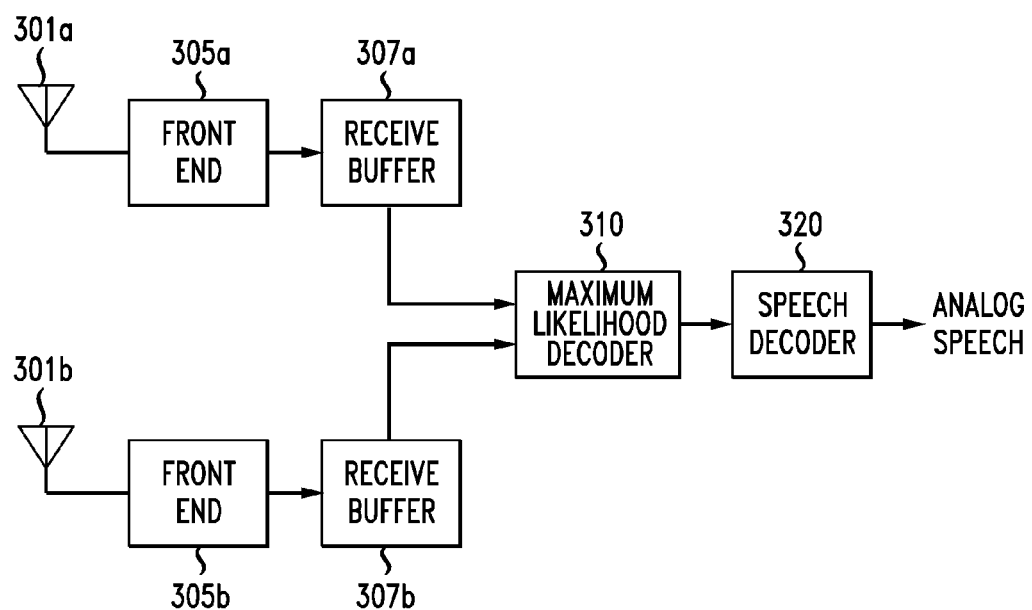
FIG. 7 illustrates a schematic block diagram of a receiver like that shown in FIG. 5, but adapted to use two antenna elements.

FIG. 7 presents an illustrative decoder in accordance with this enhancement for two receiving antennas 301a, b. As shown in the figure, received symbols from the first and second buffers associated with each antenna are provided directly to channel decoder. These are processed in a manner similar to the one described above by the decoder and a decision on the transmitted signal is made.

H. Second Illustrative Embodiment: Introduction

In the present invention, the foregoing first illustrative embodiment of the invention and its coding implementations rely upon coding technique and a delay element in the antenna transmission line, to preserve diversity and achieve additional coding gain over the simpler known delay diversity schemes. However, that illustrative embodiment can be further improved by removing the restriction that delays be introduced between different coded streams.

In particular, in the second illustrative embodiment of the invention, the inventors derive criteria for maximizing the performance when n transmit antennas are used to transmit n parallel data streams that are created by encoding information data with a channel code. In particular, it is shown that the code's performance is determined by the rank and determinant of certain matrices. These matrices in turn are constructed from codewords of the given channel code. These matrix based criteria are used to design channel codes for high data rate wireless communications. These codes are called space-time codes, and are easy to encode because they have a trellis structure. These codes can be easily decoded using maximum likelihood sequence criterion. Examples of 4PSK, 8PSK and 16QAM based codes are given that have been constructed for operation with 2 and 4 transmit antennas. Performance results are shown to verify the performance.

I. Channel Model Transmission Format: Analysis for Second Illustrative Embodiment The overall transmission channel in which the second illustrative embodiment and its coding implementation operates may be viewed as comprising n distinct channels, each illustratively undergoing independent slow (static) Rayleigh or Rician fading (it should again be understood that the principles of the present invention and this embodiment are applicable to other classes of fading channels as well), having impulse response, fade and other characteristics generally as described above for the first illustrative embodiment.

J. Second Illustrative Embodiment

Figure 8:
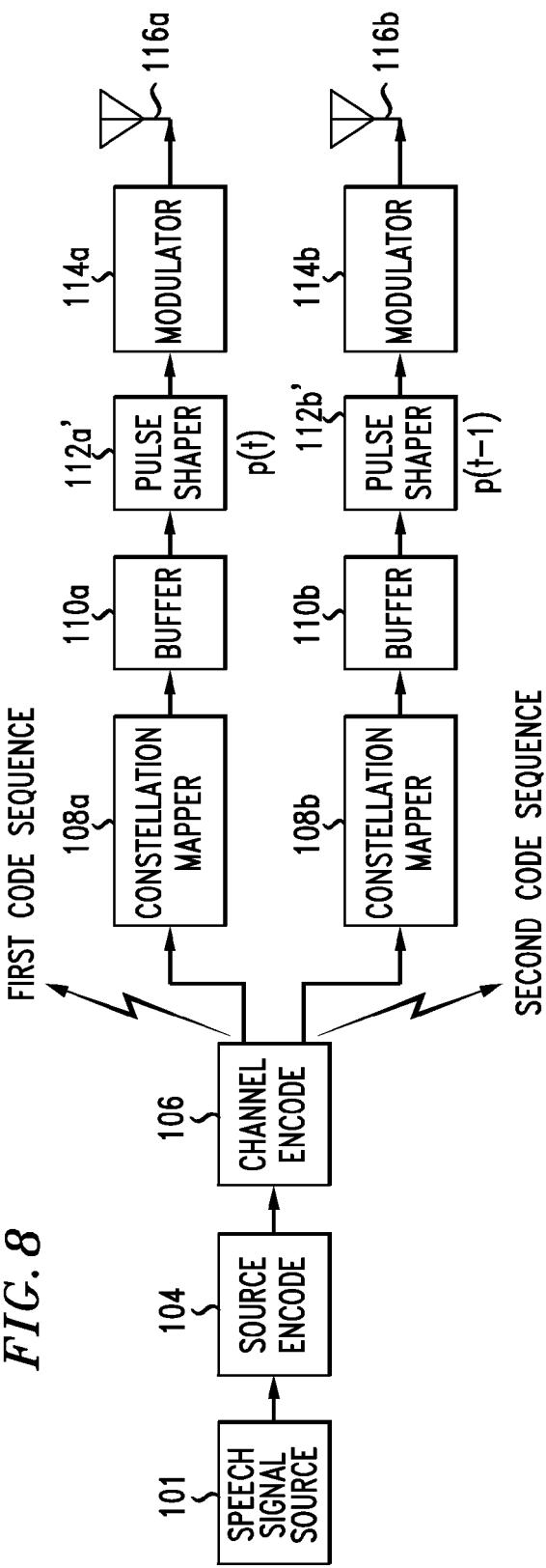
FIG. 8 illustrates a schematic block diagram of a wireless communication system constructed according to a second illustrative embodiment of the invention.

FIG. 8 presents a communication system constructed according to the second illustrative of the present invention.

The system shown is generally similar to that of the first illustrative embodiment shown in FIG. 3, and elements in common with the previous embodiment are labeled with similar numbers, including signal source 101, antennas 116a, b, encoder 104 and channel encoder 106, and constellation mappers 108a, b. It may be noted that pulse shaper 112b' in the second illustrative embodiment is not constructed to apply a delay of T, but is the same as pulse shaper 112a'.

The channel encoder 106 receives the PCM digital signal comprising a plurality of bits from the source encoder 104. Channel encoder 106 codes the PCM digital signal using a channel code that has been constructed to meet the design criteria elucidated below.

The code constructed for the second illustrative embodiment assumes that the number of antennas at the base station is two. The 4-PSK trellis code with a transmission rate of 2 bits/sec/Hz is provided for illustrative purposes in FIG. 9. Using this code, encoder 106 codes two information bits at a time to generate the label of a branch in the trellis diagram. The branch depends on the state of the encoder and the input data and determines the new state of the encoder as well. For example, suppose that the encoder is in state of FIG. 9. Then upon input bits, 00, 01, 10, and 11, the respective branch labels are respectively 30, 31, 32, and 33. The new state of the encoder is then respectively 0, 1, 2, and 3. Each branch label comprises two symbols, (see branch labels, above). Each symbol belongs to the 4-PSK constellation presented in FIG. 4(a). Thus for instance corresponding to output 31, phase values $3\pi/2$ and $\pi/2$ radians are used to phase modulate the carrier. Therefore, a coding rate of two information bits per channel used is provided by this code. Symbol 1 is transmitted with antenna 116a and symbol 2 with antenna 116b, as discussed below.

The first symbol of each codeword generated by encoder 106 is provided as input to constellation mapper 108a, and the second symbol of the codeword is provided to mapper 108b, generally as discussed above for the first illustrative embodiment.

K. Further Illustrative Channel Codes in Second Illustrative Embodiment

The second illustrative embodiment described above may employ other channel codes to enhance coding efficiency. These codes are designed according to a performance criteria computed later in the sequel. For illustration, examples are provided. One can improve on the performance of these codes by constructing encoders with more states. The inventors have designed codes (using the criteria established) with different numbers of states. Simulation results for the case of 4-PSK and 8-PSK are included demonstrating that the performance of these codes for two and one receive antenna is excellent.

L. Decoding in Second Illustrative Embodiment

Figure 10:
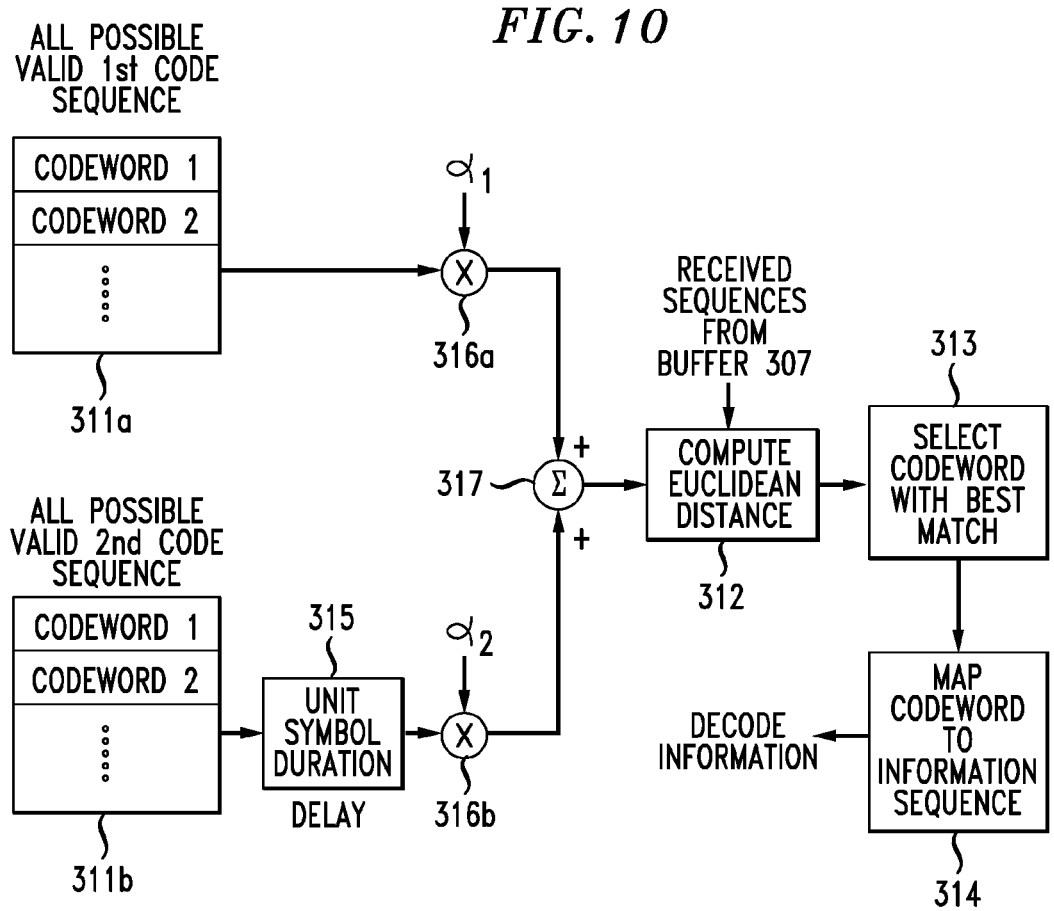
FIG. 10 illustrates a schematic block diagram of decoding circuitry used in a receiver constructed according to the second illustrative embodiment of the invention.
Figure 11:
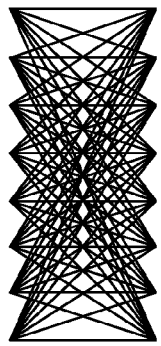
FIG. 11 illustrates an 8-PSK code, used in implementation of the second illustrative embodiment of the invention.

The second illustrative embodiment makes use of receiver 300 and related decoder circuitry illustrated in FIG. 10, generally similar to that shown in FIG. 5 described for the first illustrative embodiment. As illustrated in FIG. 10, the circuitry constructed to receive symbols from buffer 307 is adapted to account for the non-delayed coding of the second embodiment. For instance, since no delay is applied, the delay element 315 shown in FIG. 6 is not incorporated when decoding according to the second illustrative embodiment.

M. Performance Criteria for Second Illustrative Embodiment

In this section, performance criteria for the design of the codes used in the second illustrative embodiment are established.

Consider a mobile communication system such that the base station is equipped with n antennas and the mobile unit is equipped with m antennas. Data is encoded by the encoder. The encoded data goes through a serial to parallel device and is divided into n streams of data. Each stream of data is used as the input to a pulse shaper. The output of each shaper is then modulated using a modulator. At each time the output of modulator i is a signal that is transmitted using transmit antenna (Tx antenna) i for $1 \leq i \leq n$.

It is again assumed that the n signals are transmitted simultaneously each from a different transmit antenna and that all these signals have the same transmission period T. The signal at each receive antenna is a noisy version of the superposition of the faded version of the n transmitted signals.

At the receiver, the demodulator makes a decision statistic based on the received signals at each receive antenna $1 \leq j \leq m$. Assuming that the transmitted symbol from the i-th antenna at transmission interval t is $c_t^i$ the receive word at time interval t at the receive antenna j is $d_t^j$, then $$d_t^j \sum_{i=1}^{n} \alpha_i^j c_t^i + \eta_t^j \quad (3)$$

The coefficients $a_i^j$ are first modeled as independent samples of a stationary complex Gaussian stochastic process with mean $Ea_i^j = p_i^j + q_i^j j$ and variance 0.5 per dimension with $K_i^j = |Ea_i^j|^2$, where $j = \sqrt{-1}$. Tis is equivalent to the assumption that signals transmitted from different antennas undergo independent fades (The case when $a_i^j$ are dependent will be treated later). Also, $\eta_t^j$ are independent samples of a zero mean complex white Gaussian process with two sided power spectral density $N_0/2$ per dimension. It is assumed that $a_i^j$ are constant during a frame and vary from one frame to another (flat fading).

The inventors have derived a design criterion for constructing codes under this transmission scenario. Mathematical background required and the notation used for this task is first reviewed. Let $x = (x_1, x_2, \ldots, x_k)$ and $(y_1, y_2, \ldots, y_k)$ be complex vectors in the k dimensional complex space $C^k$. The inner product x and y is given by $x \cdot y = \sum_{i=1}^{k} x_i \overline{y}_i$, where $\overline{y}_i$ denotes the complex conjugate of $y_i$. For any matrix A, let A* denote the Hermitian (Transpose conjugate) of A.

From known linear algebra an n×n A is Hermitian if and only if A=A*. A is non-negative definite if $xAx^* \geq 0$ for any 1×n complex vector x. An n×n matrix V is unitary if and only if VV*=I where I is the identity matrix. A n×1 matrix B is a square root of an n×n matrix A if BB*=A. The following results from linear algebra are also made use of An eigenvector v of an n×n matrix A corresponding to eigenvalue $\lambda$ is a 1×n vector of unit Euclidean length such that $vA = \lambda v$ for some complex number $\lambda$. The number of eigenvectors of A corresponding to the eigenvalue zero is n−r, where r is the rank of A.

Any matrix A with a square root B is non-negative definite.

For any non-negative definite Hermitian matrix A, there exists a lower triangular square matrix B such that BB*=A.

Given a Hermitian matrix A, the eigenvectors of A span $C^n$, the complex space of n dimensions and it is easy to construct an orthonormal basis of $C^n$ consisting of eigenvectors A.

There exists a unitary matrix V and a real diagonal matrix D such that VAV*=D. The rows of V are an orthonormal basis of $C^n$ given by eigenvectors of A.

The diagonal elements of D are the eigenvalues $\lambda_i$, I=1, 2 . . . , n of A counting multiplicities.

The eigenvalues of a Hermitian matrix are real.

The eigenvalues of a non-negative definite Hermitian matrix are non-negative.

i. The Case of Independent Fade Coefficients

Assume that each element of signal constellation is contracted by a scale factor $\sqrt{E}$, chosen so that the average energy of the constellation element is 1. Thus the design criterion is not constellation dependent and applies equally to 4-PSK, 8-PSK and 16-QAM.

Consider the probability that the receiver decides erroneously in favor of a signal $$e = e_1^1 e_1^2 \ldots e_1^n e_2^1 e_2^2 \ldots e_2^n \ldots e_l^1 e_l^2 \ldots e_l^n$$
assuming that $$c = c_1^1 c_1^2 \ldots c_1^n c_2^1 c_2^2 \ldots c_2^n \ldots c_l^1 c_l^2 \ldots c_l^n$$
was transmitted.

Assuming ideal channel state information (CSI), the probability of transmitting c and deciding in favor of e at the decoder is well approximate by $$P(c \to e \mid \alpha_i^j, i=1, 2, \ldots, n, j=1, 2, \ldots, m) \leq \quad (4)$$
$$\exp(-d^2(c, e) E_s / 4N_0)$$

where $$d^2(c, e) = \sum_{j=1}^{m} \sum_{t=1}^{l} \left| \sum_{i=1}^{n} \alpha_i^j (c_t^i - e_t^i) \right|^2. \quad (5)$$

This is just the standard approximation to the Gaussian tail function.

Setting $\Omega_j = (\alpha_1^j, \ldots, \alpha_n^j)$, (5) is rewritten as $$d^2(c, e) = \sum_{j=1}^{m} \Omega_j A(c, e) \Omega_j^*, \quad (6)$$

where the pq in element of A(c,e) is $A_{pq} = x_p \cdot x_q$ and $x_p = (c_1^p - e_1^p, c_2^p - e_2^p, \ldots, c_l^p - e_l^p)$ for $1 \leq p, q \leq n$. Thus, $$P(c \to e \mid \alpha_i^j, i=1, 2, \ldots, n, j=1, 2, \ldots, m) \leq \quad (7)$$
$$\prod_{j=1}^{m} \exp(-\Omega_j A(c, e) \Omega_j^* E_s / 4N_0).$$

Since A(c,E) is Hermitian, there exists a unitary matrix V and a real diagonal matrix D such that VA(c,e)V*=D. The rows of V are a complete orthonormal basis of $C^n$ given by eigenvectors of A. Furthermore, the diagonal elements of D are the eigenvalues $\lambda_i$, i=1, 2, . . . , n of A counting multiplicities. The matrix $$B(c, e) = \begin{pmatrix} e_1^1 - c_1^1 & e_2^1 - c_2^1 & \cdots & e_1^1 - c_1^1 \\ e_1^2 - c_1^2 & e_2^2 - c_2^2 & \cdots & e_1^2 - c_1^2 \\ e_1^3 - c_1^3 & e_2^3 - c_2^3 & \ddots & e_1^3 - c_1^3 2 \\ \vdots & \vdots & \ddots & \vdots \\ e_1^n - c_1^n & e_2^n - c_2^n & \cdots & e_1^n - c_1^n \end{pmatrix} \quad (8)$$

is clearly a square root of A(c, e). Thus, the eigenvalues of A(c,e) are non-negative real numbers.

Let $\omega_j = \Omega_j V^*$ and $\omega_j = (\beta_1^j, \ldots, \beta_n^j)$, then $$\Omega_j A(c, e) \Omega_j^* = \sum_{i=1}^{n} \lambda_i |\beta_j^i|^2 \quad (9)$$

Next, recall that $a_i^j$ are i.i.d. samples of a complex Gaussian process with mean $Ea_i^j$ with $K_i^j|Ea_i^j|^2$. Let $K^j = (Ea_1^j, Ea_n^j)$, and let $v_w$ denote the w-th row of V.

Since V is unitary, $(v_1, v_2, \ldots, v_n)$ is an orthonormal basis of $c^n$ and $\beta_i^j$ are independent complex Gaussian random variables with variance 0.5 per dimension and mean $K^j \cdot v_i$. Let $K_{i,j} = |E\beta_i^j|^2 = |K^j \cdot v_i|^2$. Thus $|\beta_i^j|$ are independent Rician distributions with pdf $$p(|\beta_i^j|) = 2|\beta_i^j| \exp(-|\beta_i^j|^2 - K_{i,j}) I_0(2|\beta_i^j|\sqrt{K_{i,j}}).$$

for $|\beta_i^j| \geq 0$, where $I_0(\cdot)$ is the zero-order modified Bessel function of the first kind.

Thus, to compute an upper bound on the average probability of error, simply average $$\prod_{j=1}^{m} \exp(E_s/4N_0) \sum_{i=1}^{n} \lambda_i |\beta_j^i|^2)$$

with respect to independent Rician distributions of $|\beta_i^j|$ to arrive at $$P(c \rightarrow e) \leq \prod_{j=1}^{m} \left( \prod_{i=1}^{n} \frac{1}{1 + \frac{E_s}{4N_0}\lambda_i} \exp\left(-\frac{K_{i,j}\frac{E_s}{4N_0}\lambda_i}{1 + \frac{E_s}{4N_0}\lambda_i}\right) \right) \quad (10)$$

Some special cases are next examined.

The Case of Rayleigh Fading:

In this case $K_i^j = 0$ and as a fortiori $K_{i,j} = 0$ for all i and j. Then the inequality (10) can be written as $$P(c \rightarrow e) \leq \left( \frac{1}{\prod_{i=1}^{n}(1 + \lambda_i E_s/4N_0)} \right)^m. \quad (11)$$

Let r denote the rank of matrix A, then the kernel of A has dimension n−r and exactly n−r eigenvalues of A are zero. Say the nonzero eigenvalues of A are $\lambda_1, \lambda_2, \ldots, \lambda_r$, then it follows from inequality (11) that $$P(c \rightarrow e) \leq \left( \prod_{i=1}^{r} \lambda_i \right)^{-m} (E_s/4N_0)^{-rm}. \quad (12)$$

Thus a diversity of mr and a gain of $(\lambda_1, \lambda_2, \ldots, \lambda_r)^{1/r}$ is achieved. Recall that $\lambda_1, \lambda_2, \ldots, \lambda_r$, is the absolute value of the sum of determinants of all the principle r×r cofactors of A. Moreover, the ranks of A(c,e) and B(c,e) are equal. Thus from the above analysis, the following design criterion are arrived at.

Design Criteria for Rayleigh Space-Time Codes:

The Rank Criterion: In order to achieve the maximum diversity mn, the matrix B(c,e) has to be full rank for any codewords c and e. If B(c,e) has minimum rank r over the set of two tuples of distinct codewords, then a diversity of rm is achieved.

The Determinant Criterion: Suppose that a diversity benefit of rm is our target. The minimum of r-th roots of the sum of determinants of all r×r principle cofactors of A(c,e)=B(c,e)B*(c,e) taken over all pairs of distinct codewords e and c corresponds to the coding gain, where r is the rank of A(c,e). Special attention in the design must be paid to this quantity for any codewords e and c. The design target is making this sum as large as possible. If a diversity of nm is the design target, then the minimum of the determinant of A(c,e) taken over all pairs of distinct codewords e and c must be maximized.

At sufficiently high signal to noise ratios, one can approximate the right hand side of inequality (10) by $$P(c \rightarrow e) \leq \left( \frac{E_s}{4N_0} \right)^{-rm} \left( \prod_{i=1}^{r} \lambda_i \right)^{-m} \left[ \prod_{j=1}^{m} \prod_{i=1}^{r} \exp(-K_{i,j}) \right]. \quad (14)$$

Thus a diversity of rm and a gain of $$(\lambda_1, \lambda_2 \cdots \lambda_r)^{1/r} \left[ \prod_{j=1}^{m} \prod_{i=1}^{r} \exp(-Ki, j) \right]^{1/rm}$$

is achieved. Thus, the following design criteria is valid for the Rician space-time codes for large signal to noise ratios.

Design Criteria for Rician Space-Time Codes:

The Rank Criterion: This criterion is the same as that given for the Rayleigh channel.

The Gain Criterion: Let A(c,e) denote the sum of all the determinants of r×r principal co-factors of A(c,e), where r is the rank of A(c,e). The minimum of the products $$(A(c, e))^{1/r} \left[ \prod_{j=1}^{m} \prod_{i=1}^{r} \exp(-K_{i,j}) \right]^{1/rm}.$$

Taken over distinct codewords c and e have to be maximized.

Note that it has been shown that, one could still use the gain criterion f rte Rayleigh space-time codes as well, since the performance will be at least as good as the right side of inequality (11).

ii. The Case of Dependent Fade Coefficients:

Next, the case went e fade coefficients are dependent is studied. On Rayleigh fading is considered, as the Rician case can be treated in a similar manner. To this end, consider the mn×mn matrix $$Y(c,e) = \begin{pmatrix} A(c,e) & 0 & \ldots & \ldots & 0 & 0 \\ 0 & A(c,e) & \ldots & \ldots & 0 & 0 \\ 0 & 0 & A(c,e) & \ddots & \vdots & 0 \\ \vdots & \vdots & \ddots & \ddots & \vdots & \vdots \\ 0 & 0 & 0 & \ldots & 0 & A(c,e) \end{pmatrix},$$

where 0 denote the all zero n×n matrix. Let $\Omega = (\Omega_1, \ldots, \Omega_m)$, then (7) can be written as $$P(c \to e | \alpha_i^j, i=1,2,\ldots,n, j=1,2,\ldots,m) \leq \exp(-\Omega Y(c,e) \Omega^* E_s/4N_0). \tag{15}$$

Let $\theta$ denote the correlation of $\Omega$. Assume that $\theta$ is full rank (this is a physically acceptable assumption). The matrix $\theta$ being a non-negative definite square Hermitian matrix has a full rank nm×nm lower triangular matrix C as it's square root. The diagonal elements of $\theta$ are unity, so that the rows of C are of length one. Define $v=(\epsilon_1^1, \ldots, \epsilon_n^1, \epsilon_1^2, \ldots, \epsilon_n^2, \ldots, \ldots, \epsilon_1^m, \ldots, \epsilon_n^m)$ by $\Omega = vC^*$, then it is easy to see that the components of v are uncorrelated complex Gaussian random variables with variance 0.5 per dimension. The mean of the components of v can be easily computed from the mean of $a_i^j$ and the matrix C. In particular of the $a_i^j$ are of mean zero, so are the $\epsilon_i^j$.

By (15), the conclusion is arrived at that $$P(c \to e | \alpha_i^j, i=1,2,\ldots,n, j=1,2,\ldots,m) \leq \exp(-\gamma C^* Y(c,e) C \gamma^* E_s/4N_0). \tag{16}$$

The same argument can be followed as the case of independent fades with A(c,e) replaced by $C^*Y(c,e)C$. It follows that the rank of $C^*Y(c,e)C$ has to be maximized. Since C is full rank, this amounts to maximizing rank $[Y(c,e)]=m$ rank $[A(c,e)]$. Thus the rank criterion given for the independent fade coefficients holds in this case as well.

Since $a_i^j$ are zero mean, so are $\epsilon_i^j$. Thus by a similar argument to that of the case of independent fade coefficients, the conclusion that the determinant of $C^*Y(c,e)C$ must be maximized is arrived at. This is equal to det ($\theta$) det (Y(c,e))=det ($\theta$) [det (A(c,e))]$^m$. In this light the determinant criterion given in the case of independent fade coefficients holds as well.

It follows from a similar argument that the rank criterion is also valid for the Rician case and that any code designed for Rician channel performs well for Rayleigh channel even if the fade coefficients are dependent. To obtain the gain criterion, one has to compute the mean of $\epsilon_i^j$ and apply the gain criterion given in the case of independent Rician fade coefficients. As appreciated by persons skilled in the art, this is a straightforward but tedious computation.

N. Space-Time Code Construction

In this section, the results of the previous section are used to design codes for a wireless communication system that employs n transmit antennas and (optional) receive antenna diversity, according to the second embodiment of the present invention.

The designed codes can be either trellis codes, or block codes having a trellis representation. Examples are provided of trellis codes, as generalization to block codes is straightforward, to persons skilled in the art.

i. Trellis Codes

In the design of the codes to be applied in the second illustrative embodiment, reference is made to those having the property that each transition branch at time t is labeled with a sequence $q_t^1 q_t^2 \ldots q_t^n$ of n symbols from the constellation alphabet Q for all $1 \leq t \leq l$. Any time that the encoder's path goes through such a transition branch, the symbol $q_t^i$ is sent via antenna I for all $1 \leq i \leq n$.

The encoding for trellis codes is straightforward, with the exception that it is required that at the beginning and the end of each frame, the encoder be in known states. A method of decoding is illustrated next. Assuming channel estimates $\hat{a}_j^i$ of $a_i^j$, i=1, 2, n, j=1, 2, ..., m are available to the decoder. Assuming that $r_t^i$ is the received signal at receive antenna i at time t, the decoder computes for any transition branch at time t having the label $q_t^1 q_t^2 \ldots q_t^n$, the branch metric $$\sum_{j=1}^{j} \left| r_t^j - \sum_{i=1}^{n} \hat{a}_i^j q_t^i \right|^2.$$

The Viterbi algorithm is then used to compute the path with lowest accumulated metric.

The aforementioned trellis codes are called Space-Time codes, as they combine spatial and temporal diversity techniques. Furthermore, if the Space-Time code guarantee a diversity gain of rm for the multiple antenna communication systems discussed above, it is said that it is an r-Space-Time code.

Figure 9:
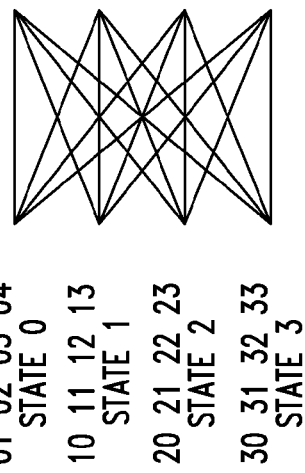
FIG. 9 illustrates a 4-PSK code, used in implementation of the second illustrative embodiment of the invention.
Figure 12A:
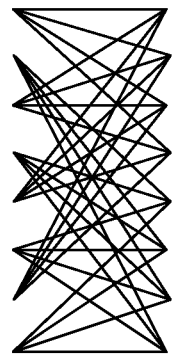
FIG. 12A-12B collectively illustrate a 4-PSK code with 8 and 16 states, used in implementation of the second illustrative embodiment of the invention.
Figure 12B:
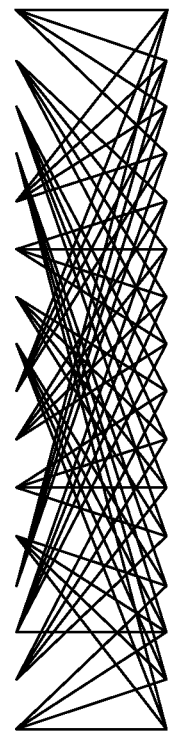
Figure 13:
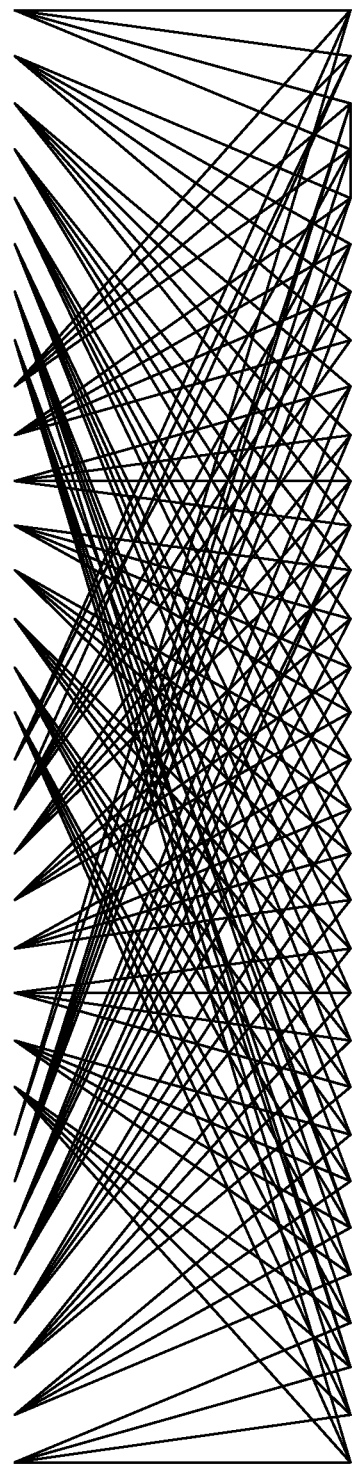
FIG. 13 illustrates a 4-PSK code with 32 states, used in implementation of the second illustrative embodiment of the invention.
Figure 14:
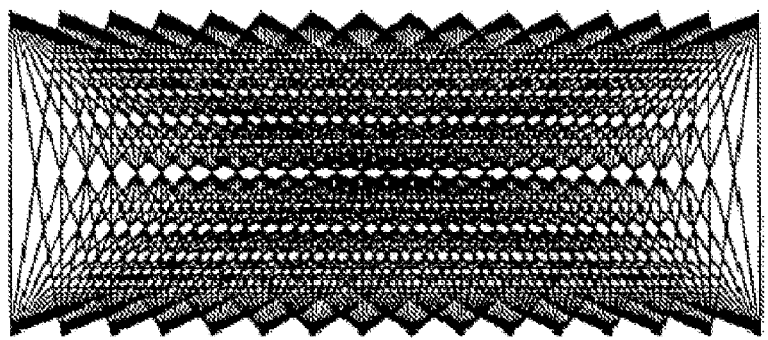
FIG. 14 illustrates a 2-Space-Time QAM code with 16 and 16 states, used in implementation of the second illustrative embodiment of the invention.

A 4-state code for the 4-PSK constellation is given in FIG. 9. For further illustration, there is also provided an 8-state code for the 8-PSK constellation in FIG. 11, and 8, 16, and 32-state codes for the 4-PSK constellation in FIGS. 12(a), 12(b), and 13, respectively. Also provided is a 16-state code for 16-QAM constellation in FIG. 14.

Figure 15:
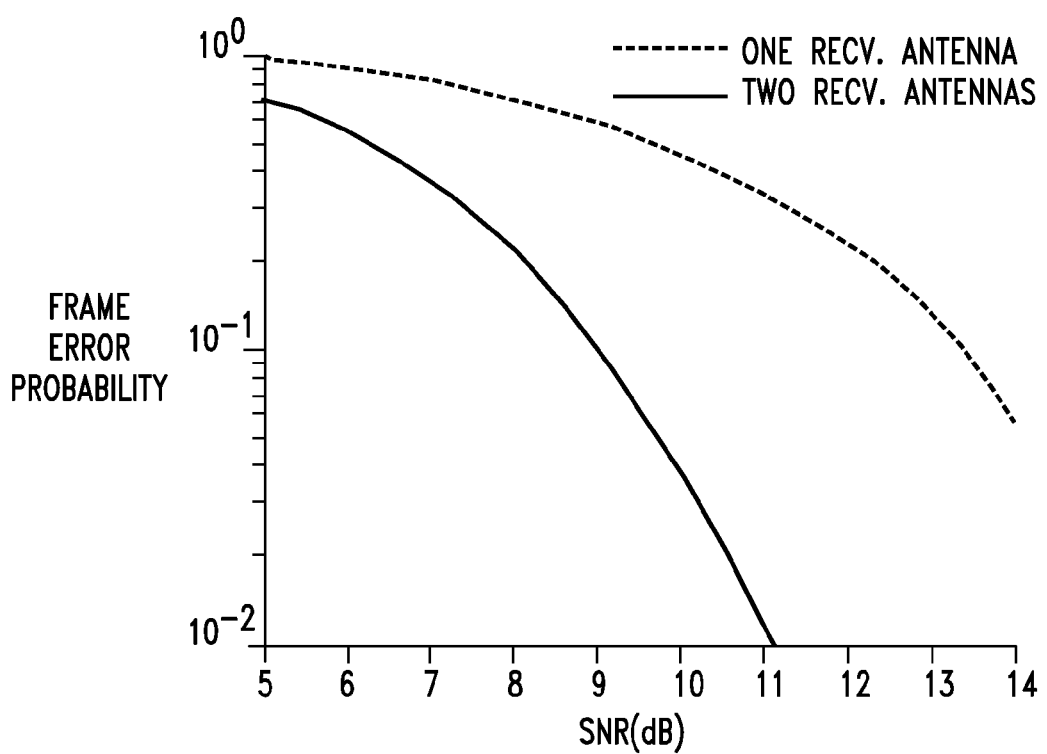
FIG. 15 illustrates data demonstrating transmission performance of transmission according to the second illustrative embodiment of the invention.

The design rules that guarantee diversity for all the codes in FIGS. 11, 12(a), 12(b), 13, and 14 are:
Transitions departing from the same state differ in the second symbol.
Transitions arriving at the same state differ in the first symbol.
r-Space-Times for $r \geq 2$:
As an illustration, a 4-space-time code for a 4 transmit antenna mobile communication systems is constructed. The input to the encoder is a block of length 2 of binary numbers corresponding to an integer i in $z_4=(0, 1, 2, 3)$. The states of the trellis correspond to set of all three tuples (s1, s2, s3) with $s_i$ in $z_4$, for $1 \leq i \leq 3$. At state (s1, s2, s3) upon receipt of input data i, the encoder outputs (i, $s_1$, $s_2$, $s_3$) elements of 4-PSK constellation (see FIG. 4(a)) and moves to state (i, $s_1$, $s_2$). The performance of this code for 1 and 2 receive antennas is given in FIG. 15.

O. Channel Estimation and Interpolation

Figure 16:
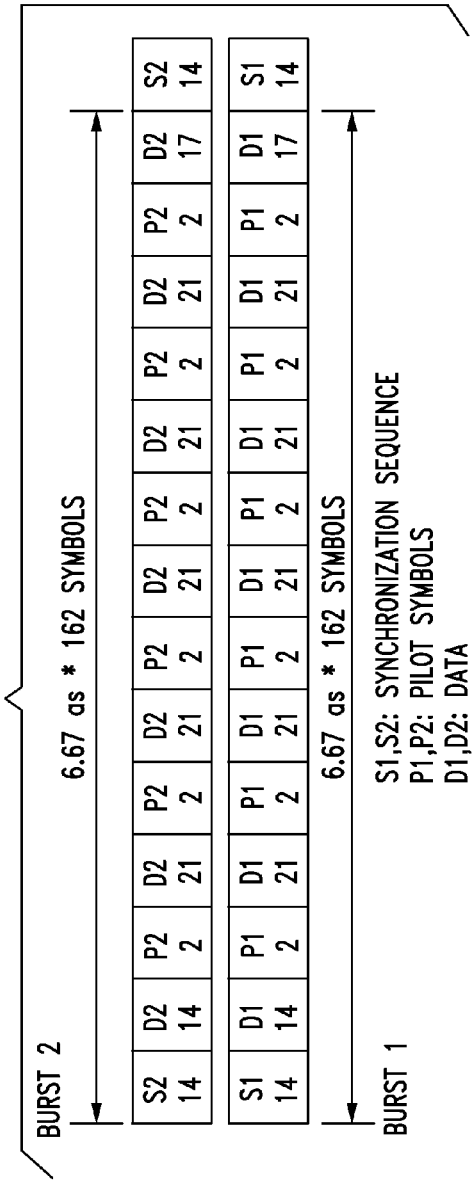
FIG. 16 illustrates a time slot structure related to channel probing techniques used in connection with the invention.

In both foregoing illustrated embodiments of the invention, it was assumed that the channel state information which is needed for decoding is known. However, in reality the receiver must estimate the channel state information. Also, the receiver must update this information as the channel varies. As illustrated in FIG. 16, this may be accomplished by the periodic transmission of a probe or pilot symbol p, whose identity is known at the transmitting and the receiving sides of the communication apparatus.

During the transmission of the pilot symbols, the receiver derives estimate of the fade coefficients. The receiver estimates the channel state over the whole frame of data using a channel interpolation scheme. The results of interpolation are used by the space-time decoder using decoding techniques known to the persons skilled in the art.

The inventors have observed that in high mobility environments inaccuracies in channel estimation and interpolation causes only a small number of errors in frames of data output by the space-time decoder. These few errors can be corrected using any outer block codes as are well-known in the art.

Her is described in implementation for a wireless modem that employs the use of space-time codes according to the invention, along with a coding strategy called concatenated space-time coding.

P. Basic Modem Architecture

In this section the basic functions of a modem based on space-time coded modulation according to the invention are described. For the purpose of illustration, the channelization of the North American digital cellular standard IS-136 is assumed. However, the same modem architecture can be easily adopted to other channelization and/or any other application with minor modifications know to people skilled in the art.

A brief overview of the frame structure in IS-136 is as follows. On each 30 kHz wireless channel, the IS-136 standard defines 25 frames of data per second, each of which is then further subdivided into 6 time slots. Each time slot is of a 6.667 ms duration and carries 162 modulation symbols (modulation symbol rate is 24,300 symbols/sec).

i). Transmitter

Figure 17:
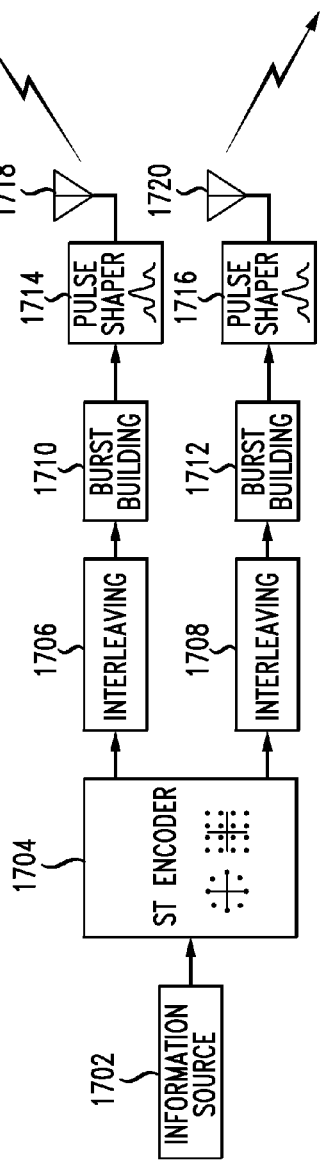
FIG. 17 illustrates a schematic diagram of a transmitter that employs space-time coding with 2 transmit antennas.

FIG. 17 shows a block diagram for a transmitter that employs space-time coding and is equipped with 2 transmit antennas (the extension of the same architecture to more than 2 transmit antennas is straightforward). A bit stream from the information source (either speech or data) is fed to the space-time encoder. The space-time encoder groups each b information bits into one modulation symbol, where the number of bits b per modulation symbols will depend on the constellation used, which is assumed to be either M-QAM or M-PSK constellation. The space-time encoder uses a space-time code constructed according to criterion mentioned above.

Each group of b information bits generates two modulation symbols at the output of the space-time encoder. Each stream of modulation symbols is interleaved using a block interleaver. It is assumed that both bursts are interleaved in a similar way. Overhead, synchronization, and pilot symbols are then added to the output of each interleaver to build a burst. Each burst is then pulse-shaped using any suitable pulse shape known to persons skilled in the art, and transmitted from its corresponding antenna.

ii). Time Slot Structure

For the purpose of illustration, FIG. 16 shows a slot structure for the case when the transmitter is equipped with two transmit antennas and follows IS-136 channelization. As mentioned, this slot structure can be easily extended to conform to other channelization and any number of transmit antennas.

In each time slot, two bursts are transmitted, one from each antenna. As in IS-136 North American Digital Cellular Standard, it is assumed that the modulation symbol rate is 24,300 symbols/sec and each burst consists of 162 symbols. Each burst starts with a 14 symbol synchronization sequence $S_1$ and $S_2$ that is used for timing and frequency synchronization at the receiver. In addition, the transmitter inserts 6 two-symbol pilot sequences $P_1$ and $P_2$ that will be used at the receiver to estimate the channel. The signal received at the receiver is the superposition of the two transmitted bursts, and in order to separate the two bursts at the receiver, it is necessary to define the two sequences $S_1$ and $S_2$ as well as the pilot sequences $P_1$ and $P_2$ as orthogonal sequences. It is assumed that the synchronization and pilot symbols have the same energy per symbol as the information symbols. In addition, for the synchronization and pilot sequences π/4-shifted DQPSK modulation is used. Each burst will then have 136 symbols of information. The block interleaver will be then a 17×8 block interleaver.

iii). Receiver

Figure 18:
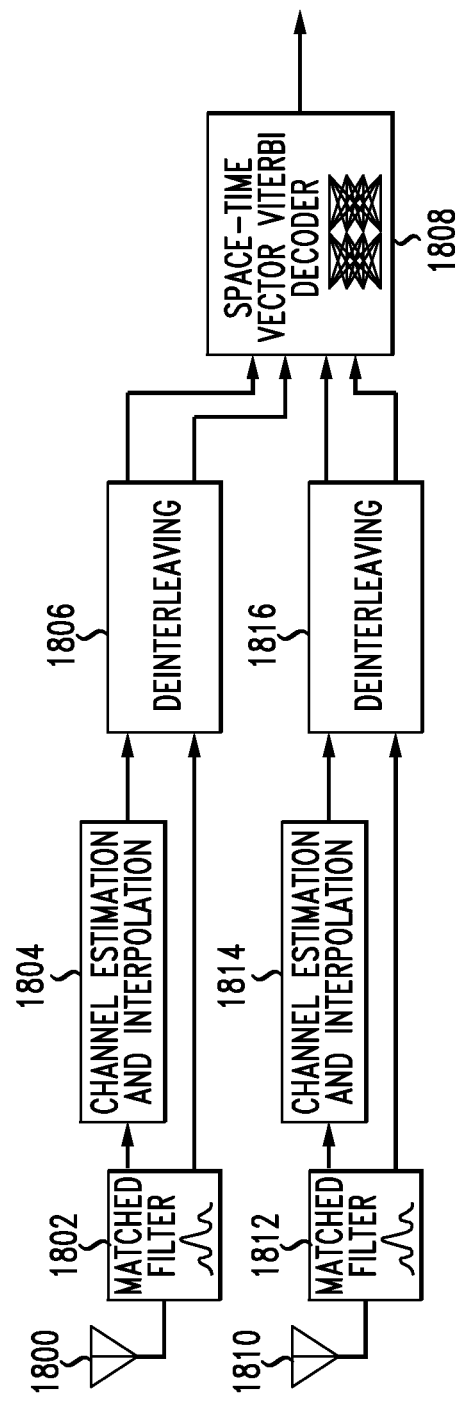
FIG. 18 illustrates a schematic diagram of the receiver with space-time vector Viterbi decoder.

FIG. 18 shows the corresponding block diagram for a mobile receiver equipped with two receive antennas according to this embodiment. For each receiver antenna, after matched filtering, the receiver splits the output samples into two streams.

The first stream contains the received samples that correspond to the information symbols. The second stream contains the received samples corresponding to the pilot symbols. These samples are first correlated with the pilot sequence for bursts transmitted from transmit antenna 1 to get an estimate for the channel (at the pilot positions) from transmit antenna 1 to the corresponding receive antenna. Also, the same set of samples are correlated with the pilot sequence for bursts transmitted from transmit antenna 2 to get an estimate for the channel (at the pilot positions) from transmit antenna 2 to the corresponding receive antenna. These estimates are then interpolated to form an estimate for channel state information needed for maximum likelihood decoding according to the metric previously defined. The interpolation filter can be designed in many ways known to persons skilled in the art. For optimum interpolation, a different interpolation filter should be used for every value of Doppler spread $f_d$, frequency offset $f_o$, and signal to noise ratio SNR. However, this approach will be of great complexity for any practical implementation. Various approaches are proposed ere. The first is to use a robust filter that will cover all possible range of operation, although this will lead to a slight degradation in performance at low Doppler and/or frequency offset values.

The second approach is to divide the range of operation into different regions, and for every region design an optimum interpolator for some operating point in that region and use that filter for the whole. By observing the channel correlation from the channel estimates or by observing the symbol error rate, the receiver can decide which filter to use for interpolation.

In addition, in estimating the channel over any burst, the pilot symbols in that burst are only used. This will minimize the overall system delay by avoiding the need to wait for future bursts in order to estimate the channel. Both data streams are then deinterleaved and fed to a vector Viterbi decoder.

iv). Basic Modem Performance

In this section, simulation results for the basic modem and time slot structure described above are presented. In addition, the pulse shape that was used is a square-root raised-cosine Nyquist pulse with roll-off factor of 0.35. At the receiver an oversampling factor of 8 is assumed.

Figure 19:
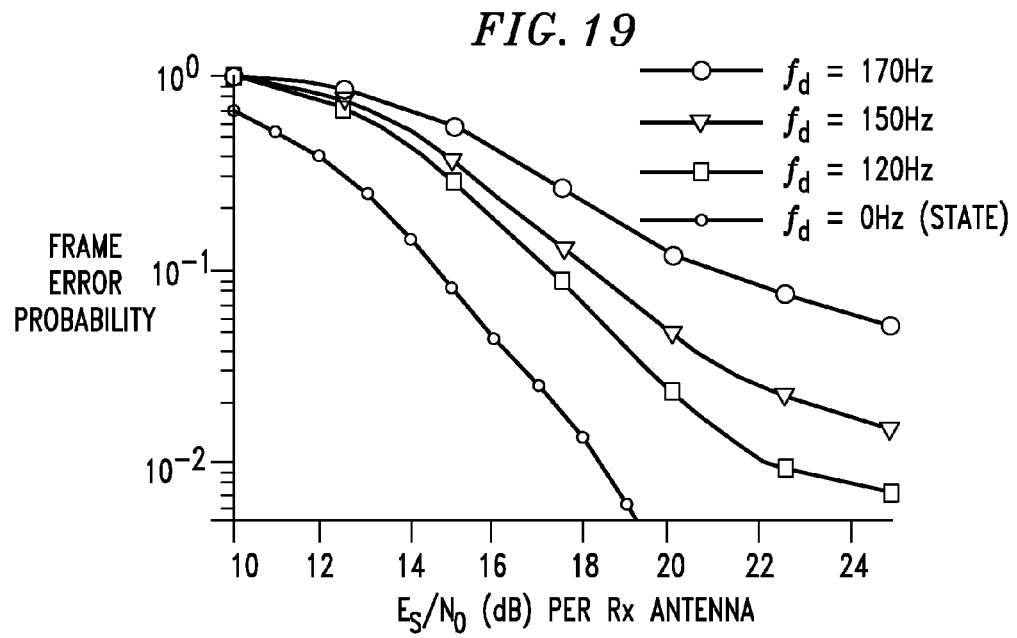
FIG. 19 illustrates the frame-error-rate performance of the basic modem structure.

FIG. 19 shows the frame error rate (FER) $P_F$ performance of the above modem for different values of Doppler spread $f_d$ assuming perfect timing and frequency synchronization. For the static case, perfect knowledge of the CSI for comparison, is assumed. Plotted is $P_F$ versus SNR (or symbol energy to noise ratio) $E_S/N_0$. For the ideal CSI, it can be seen that a FER of 0.1 at $E_S/N_0$ of 14.75 dB. However, for a Doppler spread $f_d$ of 170 Hz, which corresponds to a vehicle speed of 60 mph, the 0.1 FER is achieved t 20.5 dB $E_S/N_0$. For $f_d$=120 Hz, this number drops to 17.1 dB. It can also be noticed that FER floors at high $E_S/N_0$. In general, this increase in the required $E_S/N_0$ as compared to the case with ideal CSI and the FER flooring are due to the errors in channel estimation.

Q. Third Illustrative Embodiment-Concatenated Space-Time Coding

Figure 20:
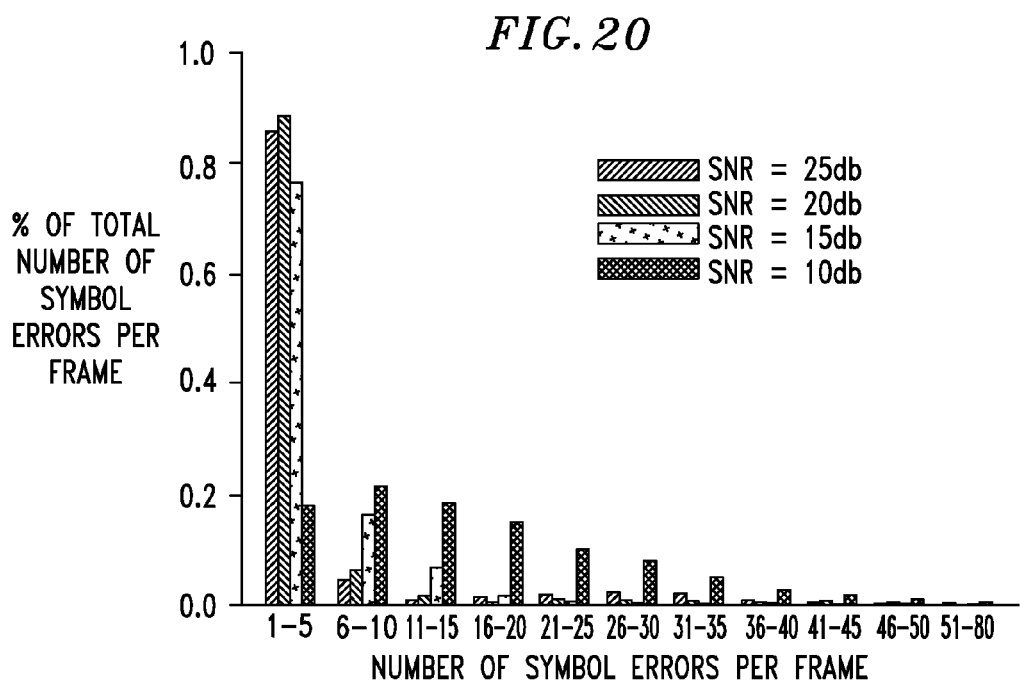
FIG. 20 shows the estimated distribution of the number of symbol errors per frame at Doppler frequency 170 Hz.
Figure 21:
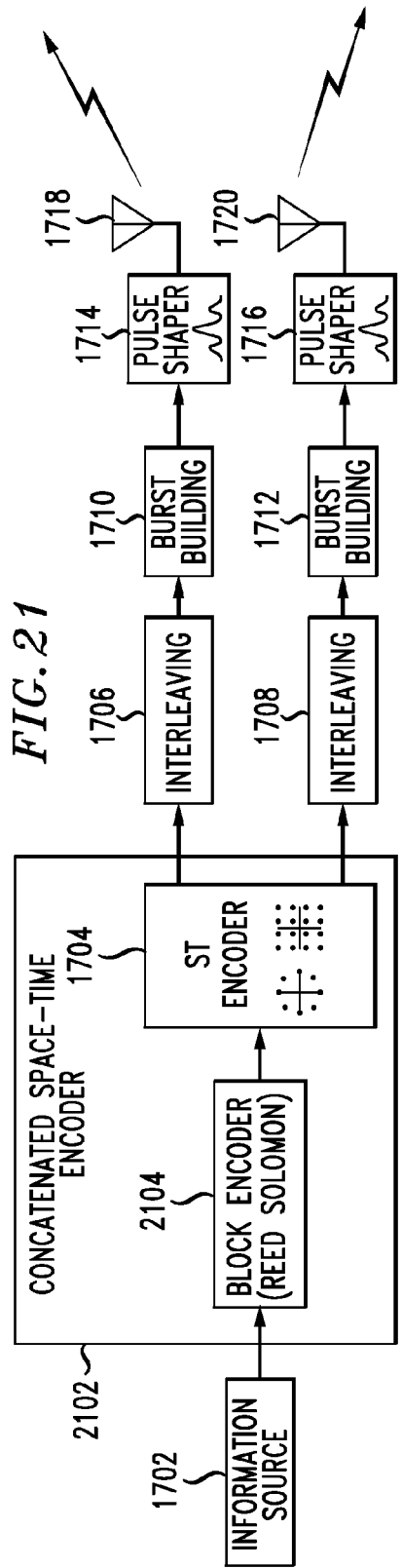
FIG. 21 illustrates a schematic diagram for the transmitter with concatenated space-time coding according to a third illustrative embodiment of the invention.
Figure 22:
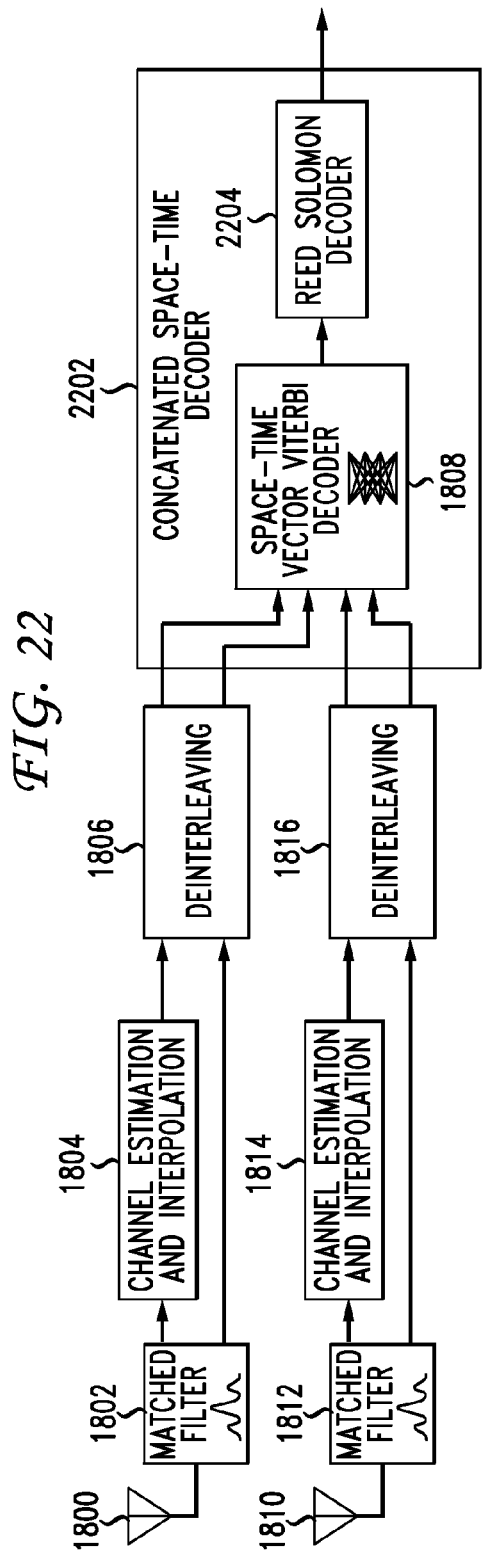
FIG. 22 illustrates a schematic diagram for the receiver with space-time vector Viterbi decoder concatenated with a Reed-Solomon decoder according to the third illustrative embodiment.

FIG. 20 shows the distribution of the number of symbol errors per frame for the $f_d$=170 Hz for different values of $E_S/N_0$. For relatively high values of $E_S/N_0$ (>15 dB), approximately 90% of the frames that are in error, the error is due to 5 symbol errors or less. Most of these errors can be recovered from, by concatenating the space-time code with any block code known to the persons skilled in the art, such as a Reed Solomon (RS) code. This overall coding strategy is designated concatenated space-time coding and is shown in FIGS. 21 and 22. Depending on the desired error correction capability and rate of the code and the type of constellation used, the dimension of the block code used should be such to produce an integer multiple of modulation symbols for each RS symbol. In this way, it will be possible to decode a burse immediately without the need to wait for other bursts and, thereby, minimize decoding delay. In addition, in this way, any symbol error at the output of the ST decoder will affect only one RS code symbol.

R. Modem Performance with Concatenated Space-Time Coding

The inventors simulated the above-described modem with the space-time code concatenated with a Reed-Solomon code. Three different shortened RS codes over $GF(2^8)$ symbols are first created by partitioning the bit stream into 66 groups of 8 bits each. The output 68 $GF(2^8)$ symbols are then partitioned into 136 16-QAM symbols, 2 channel symbols per one Reed-Solomon code, referred to as RS3, is a shortened (68, 62) code that corrects three byte errors, and the third code, referred to as RS5, is a shortened (68,58) code that corrects 6 byte errors. In this simulation, a timing error of ±T/16 and a frequency offset $f_o$ of 200 Hz are assumed.

Figure 23:
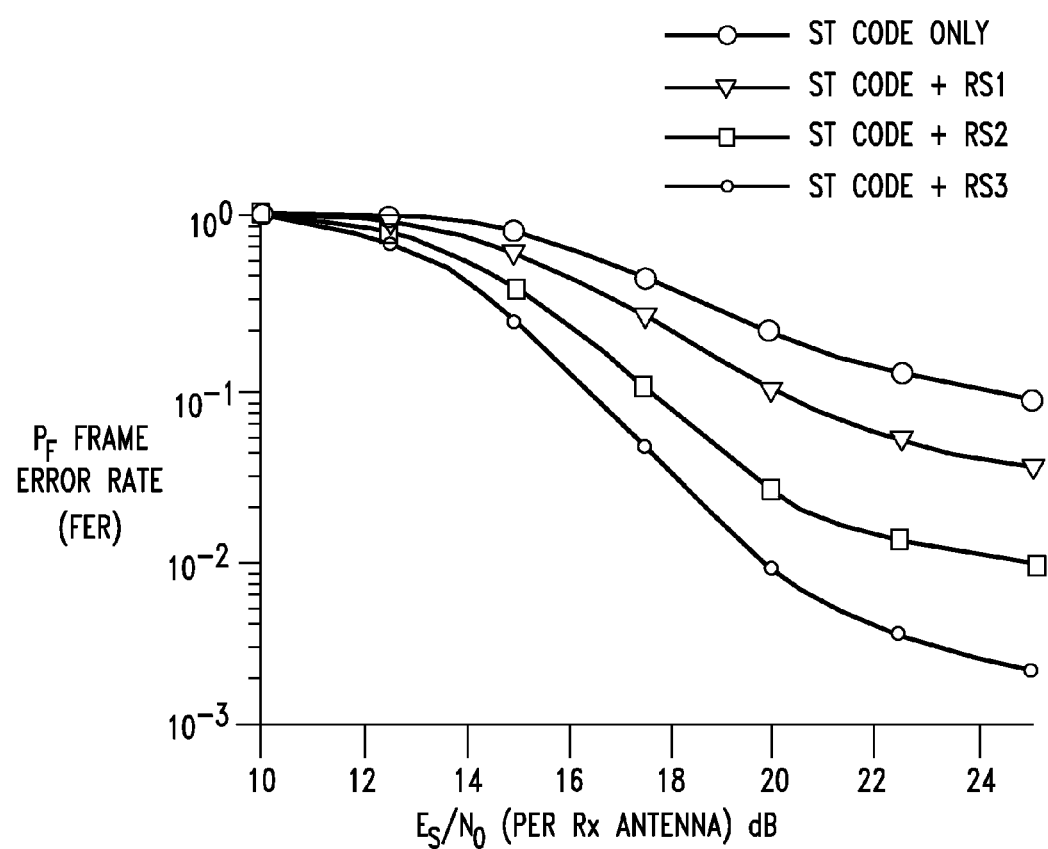
FIG. 23 illustrates the performance of the concatenated space-time code of the third illustrative embodiment of the invention.

FIG. 23 shows the FER performance with concatenated space-time coding and in the presence of timing error and frequency offset for $f_d$=170 Hz. From this figure, it can be seen that in the case of the ST code alone a $E_S/N_0$ of 23 dB is required to achieve $P_F$ of 0.1. However, when the ST code is concatenated with RS3, for example, the required $E_S/N_0$ is 17.5 dB, i.e., a 5.5 dB gain over the ST code alone. However, in this case, the net bit rate (per 30 kHz channel) will be reduced from 81.6 kbits/sec to 74.4 kbits/sec. If RS5 is used, the required $E_S/N_0$ for $P_F$=0.1 will drop to 16.5 dB, which is only 1.75 dB higher than the case when ideal CSI are available. In this case, the net bit rate will be 69.6 kbits/sec.

S. Fourth Illustrative Embodiment—Multi Level Structured Space Time Codes

Some of the space-time codes described in the second embodiment of this invention may have multilevel structure. On occasions, it may be desirable to take advantage of this structure in practical communication systems, particularly when the number of transmit antennas is high. This has the significant advantage of reducing decoding complexity. Multilevel code structures and associated decoding techniques are known in the art. They can be combined with space-time coding, giving rise to the invention of a novel technique called multi-level space-time coding.

Without loss of generality, assume that the signal constellation $Q_0$ consists of $2^{b_0}$ points. Assume that f-levels of coding is used. Associated with this f-levels of coding, a partition based on subsets $$Q_{f-1} \subset Q_{f-2} \subset \ldots Q_1 \subset Q_0$$

is chosen with the number of elements of $Q_j$ equal to $2^{b_j}$ for all $0 \le j \le f-1$. By such a partitioning, it is meant that $Q_0$ is the union $2^{b_0-b_1}$ disjoint sets called cosets of $Q_1$ in $Q_0$, each having $2^{b_1}$ elements such that one of these cosets is $Q_1$. Having the cosets of $Q_1$ in $Q_0$ at hand, each coset is then divided into $2^{b_1-b_2}$ disjoint sets each having $2^{b_2}$ elements. The $2^{b_1-b_2}$ subsets of $Q_1$ are called cosets of $Q_2$ in $Q_1$. The set of cosets of $Q_2$ in $Q_1$ must include $Q_2$. Thus there are $2^{b_0-b_2}$ subsets of $Q_0$ with $2^{b_2}$ elements called the cosets of $Q_2$ in $Q_0$. The set of cosets of $Q_2$ in $Q_0$ includes $Q_2$. This procedure is repeated until cosets of $Q_j$ in $Q_k$ for all $0 \le k \le j < f-1$ are arrived at. Let $r_{f-1}=b_{f-1}$ and $r_j=b_{j+1}-b$, for $j=0, 1, \ldots f-2$. Then $Q_j$ contains $2^{r_j}$ cosets of $Q_{j+1}$ for all $j=0, 1, \ldots, f-2$.

Every $K=K_0+\ldots+K_{f-1}$ bits of input data is encoded using encoders $0, 1, \ldots, f-1$ corresponding to the f levels. It is required that all the encoders have a trellis representation. At each time t depending on the state of the j-th encoder and the input data, a branch of the trellis of the j-th encoder is chosen which is labeled with n blocks of $r_j$ bits denoted by $B_t^i(j)$, $B_t^2(j), \ldots, B_t^n(j)$. The blocks $B_t^i(0), \ldots, B_t^i(f-1)$ then choose a point of the signal constellation in the following way.

The block $B_t^i(0)$ chooses a coset $Q_1'$ of $Q_1$ in $Q_0$. The block $B_t^i(1)$ chooses a coset $Q_2'$ of $Q_2$ in $Q_1$ and so forth. Finally, the block $B_t^i(f-1)$ chooses a point of $Q'_{f-1}$ a coset of $Q_{f-1}$ chosen in the last step. The chosen point is then transmitted using the i-th antenna for $1 \le i \le n$. Multilevel decoding can be done in a manner known to those skilled in the art.

Suppose that the encoder of the j-th level has $2^{s_j}$ states at time t. One can view the multi-level code described above as a space-time code C with $2^{(s_0+\ldots+s_{f-1})}$ states at time t. The states of C correspond f-tuples $(s_t^0, s_t^1, \ldots, s_t^{f-1})$ states of encoders $0, 1, \ldots, f-1$. The branch labels between states $(s_t^0, s_t^1, \ldots, s_t^{f-1})$ and $(s_{t+1}^0, s_{t+1}^1, \ldots, s_{t+1}^{f-1})$ is the set of symbols that are sent via antennas $1, 2, \ldots, n$ if each encoder j goes from states $s_t^j$ for $0 \le j \le f-1$. In this way, one can view a multi-level space-time code as a regular space-time code with a multi-level structure that allows simplified decoding. The penalty for this simplified decoding is loss in performance. Also, the design criterion derived previously could be applied to the space-time code C. Alternatively the design criteria can instead by applied to the trellis of each encoder $0 \le j \le f-1$ providing different diversities at each level.

Figure 24:
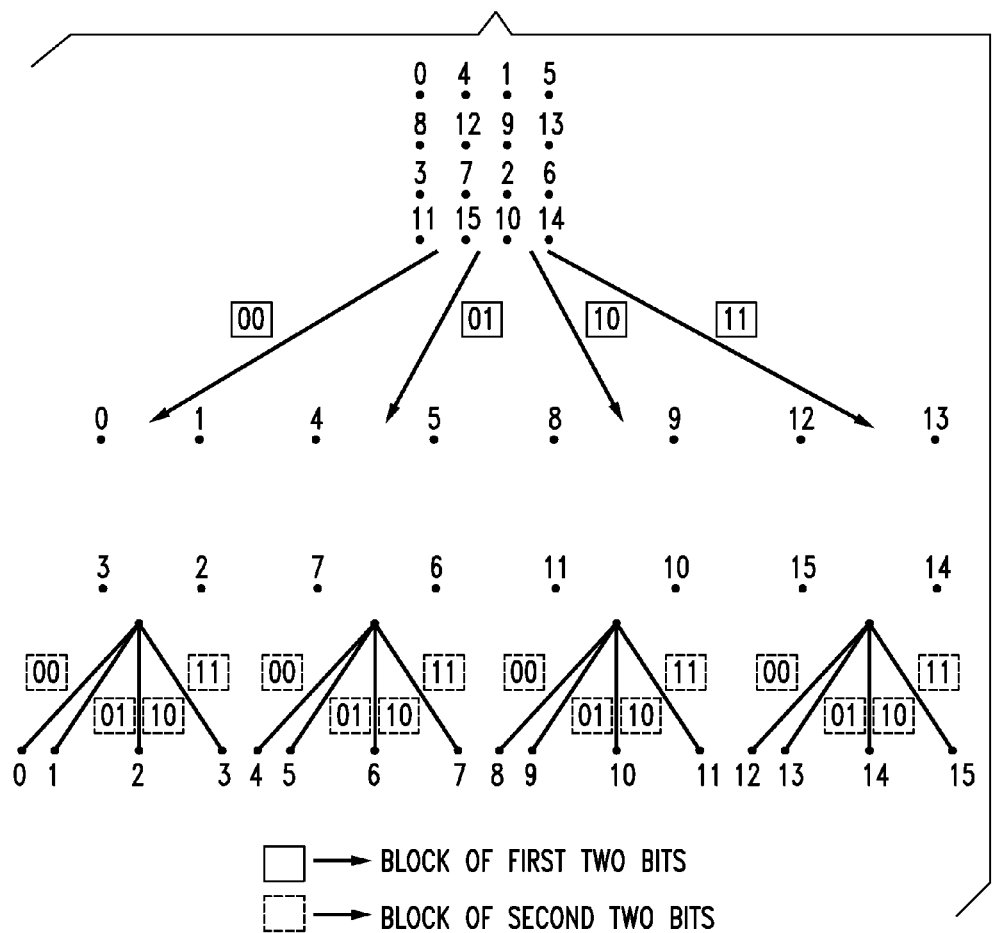
FIG. 24 describes set partitioning of a 16 QAM constellation to be used in an example of multi-level space-time codes according to the fourth illustrative embodiment of the invention.
Figure 25:
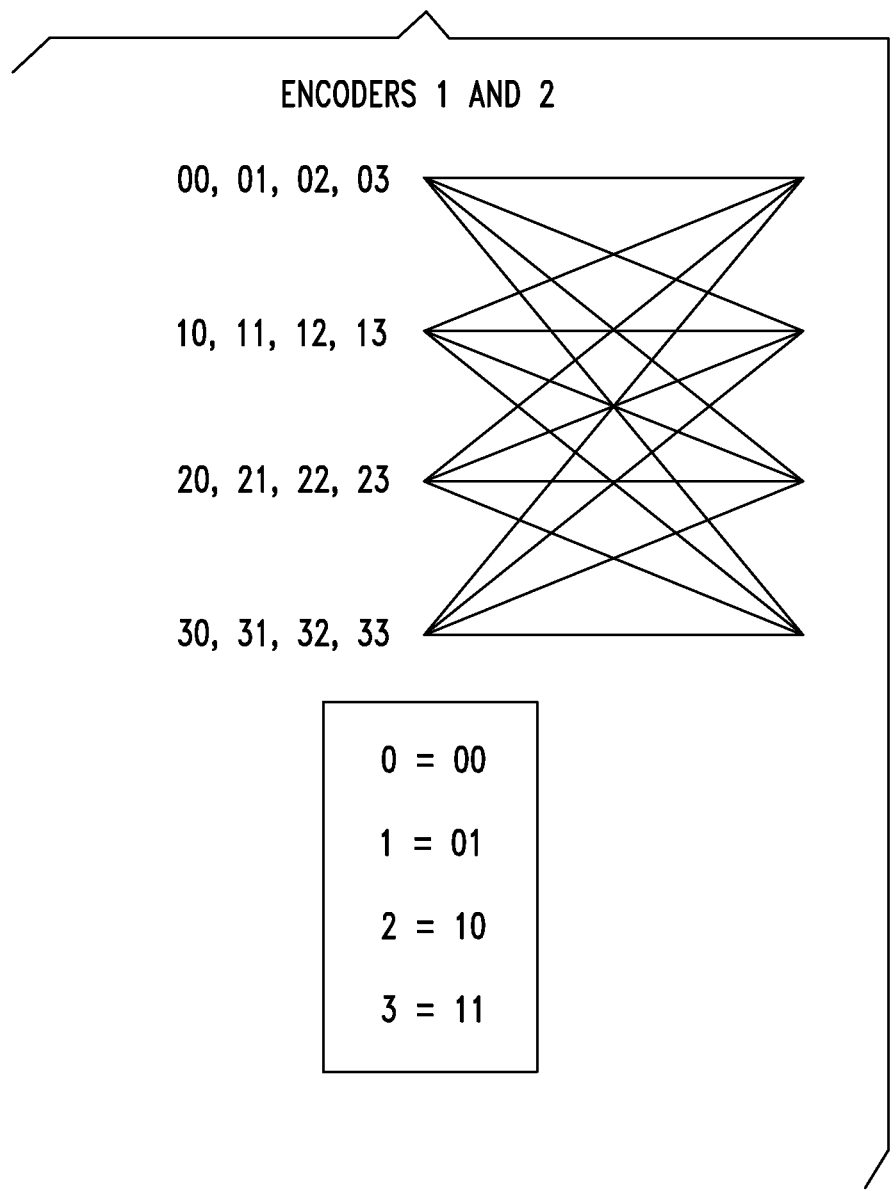
FIG. 25 describes example of encoders for different levels of multi-level space-time code.
Figure 26:
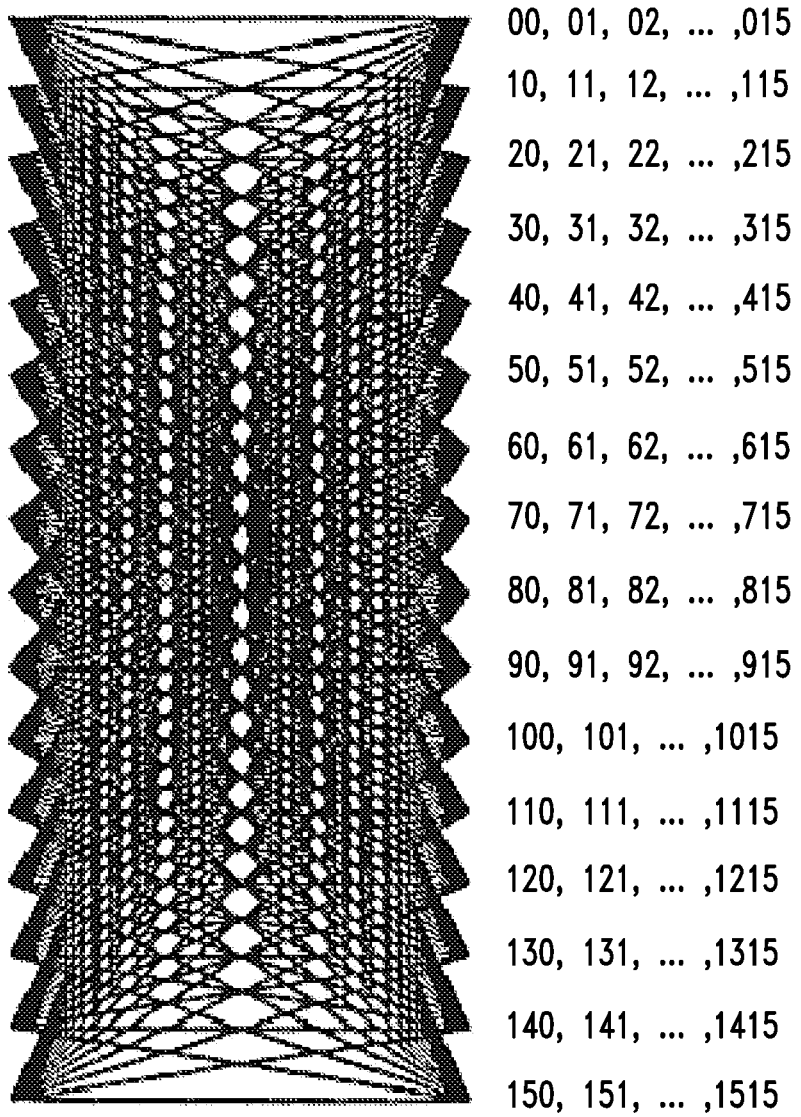
FIG. 26 describes an equivalent space-time code for an example of a multi-level space-time code constructed according to the fourth illustrative embodiment of the invention.

The discussion of the illustrative embodiment above is illustrated with an example. Consider the transmission of 4-bits/sec/HZ using the 16-QAM constellation and the set partitioning of FIG. 24. At each time input bits are grouped into two blocks of two bits. The first and second blocks of two bits input data are respectively the input to the first and second encoder whose trellis is given in FIG. 25. Each branch of the trellis is labeled with two blocks of two bits of data. These two bits are represented with numbers 0, 1, 2 and 3. Upon the choice of branches with respective labels $a_1a_2$ and $b_1b_2$ by the zero-th and the first encoders, the signal points $4a_1+b_1$ and $4a_2+b_2$ are sent via antennas 1 and 2. The equivalent 16-state space-time trellis code is given in FIG. 26.

T. Fifth Illustrative Embodiment—Smart-Greedy Codes

Smart greedy codes are a class of space-time codes of particular interest in the implementation of the invention. These codes are able to take special advantage of possible rapid changes in the channel without any feedback from the receiver. The idea is to construct codes using a hybrid criteria such that possible rapid changes in the channel is taken into account by the design criteria. In this light, an analysis is provided for the case of rapidly fading channels as well.

i) Analysis of Rapid Fading

In this connection, the model of a mobile communication system having n antennas at the base and m antennas at the mobile station is refined. Data is encoded using a channel code. As in other embodiments, the encoded data goes through a serial to parallel device and is divided into n streams of data. Each stream of data is used as the input to a pulse shaper. The output of each shaper is then modulated using a modulator. At each time the output of modulator I is a signal that is transmitted using transmit antenna (Tx antenna) I for $1 \leq i \leq n$. Again, the n signals are transmitted simultaneously each from a different transmit antenna and all these signals have the same transmission period T. The signal at each receive antenna is a noisy version of the superposition of the faded versions of the n transmitted signals. Assume that each element of the signal constellation is contracted by a scale factor $\sqrt{E_s}$ chose so that the average energy of the constellation is 1.

At the receiver, the demodulator makes decision statistic based on the received signals at each receive antenna $1 \leq j \leq m$. Let $c_t^i$ denote the transmitted symbol from the i-th transmit antenna at transmission interval t and $d_t^j$ be the receive word at the receive antenna j. Then, $$d_t^j = \sum_{i=1}^{n} \alpha_i^j(t) c_t^i \sqrt{E_s} + \eta_t \quad (18)$$

This is equivalent to the assumption that signals transmitted from different antennas undergo independent fades. The coefficients $\alpha_i^j(t)$ are modeled as samples of a stationary complex Gaussian stochastic process with mean zero and variance 0.5 per dimension. Also, $\eta_t^j$ are independent samples of a zero mean complex white Gaussian process with two sided power spectral density $N_0/2$ per dimension. For the static fading case, support that $\alpha_i^j(t)$ are constant during a frame and are independent from one frame to another and a design criterion was established. When the fading is rapid, the coefficients $\alpha_i^j(t)$, t+1, 2, ..., 1, i=1, 2, ..., n, j=1, 2, ..., m are modeled as independent samples of a complex Gaussian process with mean zero and variance 0.5 per dimension, and another design criteria is established as follows.

Assuming that the coefficients $\alpha_i^j(t)$ for t=1, 2, ..., 1, i=1, 2, ..., n, j=1, 2, ..., m are known to the decoder, the probability of transmitting $$c = c_1^1 c_1^2 \ldots c_1^n c_2^1 c_2^2 \ldots c_2^n \ldots c_l^1 c_l^2 \ldots c_l^n,$$

and deciding in favor of $$e = e_1^1 e_1^2 \ldots e_1^n e_2^1 e_2^2 \ldots e_2^n \ldots e_l^1 e_l^2 \ldots e_l^n$$

at the decoder is well approximated by $$P(c \to e \mid \alpha_i^j, i = 1, 2, ..., n, j = 1, 2, ..., m, t = 1, 2, ..., l) \leq$$
$$\exp(-d^2(c, e) E_s / 4 N_0)$$

where $$d^2(c, e) = \sum_{j=1}^{m} \sum_{t=1}^{l} \left| \sum_{i=1}^{n} \alpha_i^j(t)(c_t^i - e_t^i) \right|^2 \quad (19)$$

This is the standard approximation to the Gaussian tail function.

Let $$\Omega_j(t) = (\alpha_1^j(t), \alpha_2^j(t), \ldots, \alpha_n^j(t))$$

and C(t) denote the n×n matrix with the element at p-th row and q-th column equal to $(c_t^p - e_t^p)(\overline{c}_t^q - \overline{e}_t^q)$. Then it can be seen that $$d^2(c, e) = \sum_{j=1}^{m} \sum_{t=1}^{l} \Omega_j(t) C(t) \Omega_j^*(t) \quad (20)$$

The matrix C(t) is Hermitian, thus there exist a unitary matrix V(t) and a diagonal matrix D(t) such that C(t)=V(t)D(t)V*(t). the diagonal elements of D(t), denoted here by $D_{ii}(t)$, $1 \leq i \leq n$, are the eigenvalues of C(t) counting multiplicities. Such C(t) is Hermitian, these eigenvalues are real numbers. Let $$\Lambda_j(t) = \Omega_j(t) V(t) = (\lambda_1^j(t), \ldots, \lambda_n^j(t)),$$

then $\lambda_i^j(t)$ for i=1, 2, ..., n, j=1, 2, ..., m, t=1, 2, ..., 1 are independent complex Gaussian variables with mean zero and variance 0.5 per dimension and $$\Omega_j(t) C(t) \Omega_j^*(t) = \sum_{i=1}^{n} |\lambda_i^j(t)|^2 D_{ii}(t).$$

By combining this with (19) and (20) and averaging with respect to the Rayleigh distribution of $|\lambda_i^j(t)|$, the following is arrived at $$P(c \to e) \leq \prod_{i,t} \left(1 + D_{ii}(t) \frac{E_s}{4N_0}\right)^{-m}. \quad (21)$$

The matrix C(t) is next examined. The columns of C(t) are all different multiples of $$c_t - e_t = (c_t^1 - e_t^1, c_t^2 - e_t^2, \ldots, c_t^n - e_t^n).$$

Thus C(t) has rank 1 if $c_t^1 c_t^2 \ldots c_t^n \neq e_t^1 e_t^2 \ldots e_t^n$ and rank zero otherwise. It follows that n−1 elements in the list $$D_{11}(t), D_{22}(t), \ldots, D_{nn}(t)$$

Are zeros and the only possible nonzero element in this list is $|c_t - e_t|^2$. By (21), it can be concluded that $$P(c \to e) \leq \prod_{t=1}^{l} \left(1 + |c_t - e_t| 2 \frac{E_s}{4N_0}\right)^{-m} \quad (22)$$

Let $V(c,e)$ denote the set of time instances $1 \leq t \leq 1$ such that $|c_t - e_t| \neq 0$ and let $|V(c,e)|$ denote the number of elements of $v(c,e)$. Then it follows from (22) that $$P(c \to e) \leq \prod_{t \in v(c,e)} \left( |c_t - e_t| 2 \frac{E_s}{4N_0} \right)^{-m}. \quad (23)$$

It follows that a diversity of $m|V(c,e)|$ is achieved. Examining the coefficient of $(E_s/4N_0)^{-mV(c,e)}$ leads to the desired design criterion. Below, this criterion is combined with that of static flat fading case given before to arrive at a hybrid criteria.

U. A Hybrid Design Criteria for Smart Greedy Space-Time Codes

The Distance/Rank Criterion:

In order to achieve the diversity vm in a rapid fading environment, for any two code words c and e the strings $c_t^1 c_t^2 \ldots c_t^n$ and $e_t^1 e_t^2 \ldots e_t^n$ must be different at least for u values of $1 \leq t \leq n$. Furthermore, let $$B(c,e) = \begin{pmatrix} e_1^1 - c_1^1 & e_2^1 - c_2^1 & \ldots & e_t^1 - c_t^1 \\ e_1^2 - c_1^2 & e_2^2 - c_2^2 & \ldots & e_t^2 - c_t^2 \\ e_1^3 - c_1^3 & e_2^3 - c_2^3 & \ddots & e_t^3 - c_t^3 \\ \vdots & \vdots & \ddots & \vdots \\ e_1^n - c_1^n & e_2^n - c_2^n & \ldots & e_t^n - c_t^n \end{pmatrix}$$

If $B(c,e)$ has minimum rank r over the set of pairs of distinct codeword, then a diversity of rm is achieved in static flat fading environments.

The Product/Determinant Criterion:

Let $V(c,e)$ denote the set of time instances $1 \leq t \leq 1$ such that $c_t^1 e_t^2 \ldots c_t^n \neq e_t^1 e_t^2 \ldots e_t^n$ and let $$|c_t - e_t|^2 = \sum_{i=1}^n |c_t^i - e_t^i|^2.$$

Then to achieve the most coding gain in a rapid fading environment, the minimum of the products $\prod_{t \in v(c,e)} |c_t - e_t|^2$ taken over distinct codewords e and c must be maximized. For the case of a static fading channel, the minimum of r-th roots of the sum of determinants of all r×r principal cofactors of $A(c,e) = B(c,e)B^*(c,e)$ taken over all pairs of distinct codewords e and c corresponds to the coding gain, where r is the rank of $A(c,e)$.

The construction of illustrative implementations of smart greedy codes according to this embodiment of the invention is illustrated with some examples. It will be assumed that at the beginning and the end of the frame, the encoder is in the zero state.

Example A

Figure 27A:
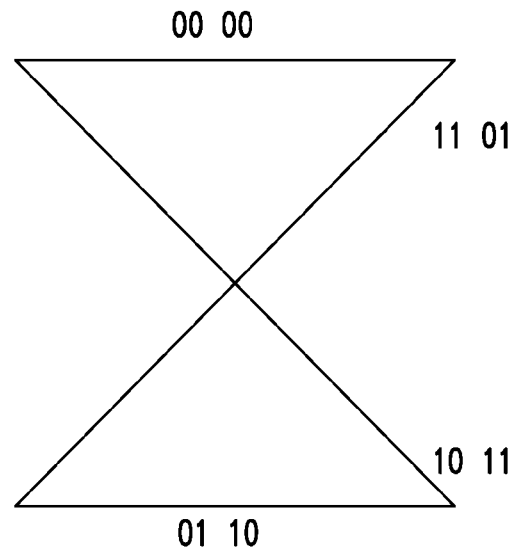
FIGS. 27(a) and 27(b) respectively illustrate smart greedy codes constructed using the BPSK and 4-PSK constellations, according to a fifth illustrative embodiment of the invention.

Suppose that a transmission rate of 0.5 bits/sec/Hz is required. In this example and as illustrated in FIG. 27(a), the BPSK constellation is used, with 0 denoting $\sqrt{E_s}$ and 1 denoting $\sqrt{E_s}$. The objective is to guarantee diversity gains 2 and 4 respectively in slow and rapid flat fading environments. The following code using M-TCM construction guarantees these diversity gains. At any time $2K+1$, $k=0, 1, 2, \ldots$ depending on the state of the encoder and the input bit a branch is chosen by the encoder and the first coordinate and second coordinates of the labels are sent simultaneously from Tx antennas at times $2k+1$ and $2K+2$. For instance at time 1, if the branch label 10 11 is chosen, symbols 1,0 and 1,1 are sent respectively from transmit antennas one and two at times one and two.

Example B

Figure 27B:
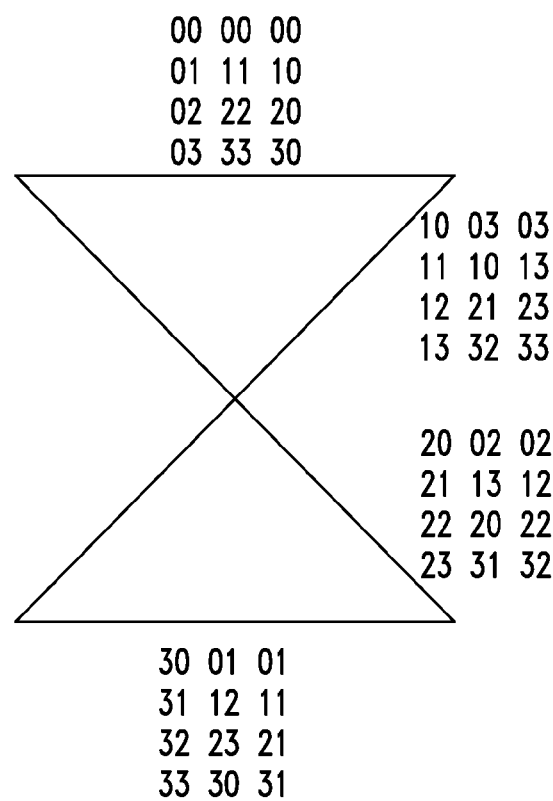

Here a transmission rate of 1 bits/secs/Hz and diversity gains of 2 and 3 respectively in static and rapid flat fading environments are desired. In this example, illustrated in FIG. 27(b), the 4-PSK constellation is used instead. The objective is to guarantee diversity gains 2 and 3 respectively in slow and rapid flat fading environments. The following code using M-TCM construction guarantees these diversity gains. At times $t=3k$, $k=0, 1, 2, \ldots$, three bits of data arrive at the encoder. The first bit choose a branch depending on the state of the encoder and the rest of two bits choose one of the 4 labels of that branch such as $b_t^1 b_t^2 b_{t+1}^1 b_{t+1}^2 b_{t+2}^1 b_{t+2}^2$. Then $b_t^1$, $b_{t+1}^2$ and $b_{t+2}^1$ are sent via antenna 1 respectively at times t, t+1 and t+2. Similarly, $b_t^2$, $b_{t+1}^2$ and $b_{t+2}^2$ are sent via antenna 2 respectively at time t, t+1 and t+2.

As before, the inventors have simulated the performance of communication systems designed based on the above code. Excellent results have been confirmed in both fast and slow fading environments.

The foregoing description of the system and method of the invention is illustrative, and variations in construction and implementation will occur to persons skilled in the art. For example, although the present invention is described in the time domain, frequency domain analogs or variants of it easily occur to those skilled in the art. For instance, space-time codes presented in the second illustrative embodiment can be easily applied to DS-CDMA communication systems. To illustrate, assume that user X is provided with two transmit antennas (with generalization to n antennas being trivial to those skilled in the art). User X chooses a space-time code designed to be used with two transmit antennas. User X can use a similar PN sequence for data transmission from both antennas. At the receiver side, correlation with the aforementioned sequence gives a sum of faded versions of the signals transmitted from each antenna. In this light, decoding of the space-time code can be carried out in a manner similar to those described in the second embodiment of this work as well.

Alternatively, user X can use distinct PN sequences for transmission from both transmit antennas. If the PN sequences used to transmit from both antennas are orthogonal to each other, at the receiver co-relation with the first or second sequence gives respectively noisy versions of the transmitted signals from antennas one or two, which can be used for decoding at the receiver. This has a penalty in terms of bandwidth expansion but can be used to increase the data rate and/or provide diversity advantage.

In general, it is also possible to choose two arbitrary PN sequences for two transmit antennas. Correlation with these sequences at the receiver side gives sums of faded versions of multiples of the transmitted signals that can be used for decoding.

The above discussion demonstrates a DS-CDMA analog of the space-time coding. Analogs of the embodiments of the present invention in frequency domain also can easily be obtained, but are not discussed here.

For further instance, while mobile cellular implementations have been described, the invention could be applied to other communication environments. The invention is accordingly intended to be limited only by the following claims.

We claim:

1. A method comprising:
   converting each group of successive groups of k incoming bits into a first sequence of symbols and a second sequence of symbols;
   modulating a carrier using the first sequence of symbols to generate a first modulated signal;
   transmitting the first modulated signal from a first transmitting antenna; and
   transmitting a second modulated signal from a second transmitting antenna, wherein the second modulated signal is generated using the second sequence of symbols, and wherein the first transmitting antenna differs from the second transmitting antenna.

2. The method of claim 1, wherein the first sequence of symbols and the second sequence of symbols are different from one another, forming a space-time diversity mapping between the incoming bits and the first sequence of symbols and the second sequence of symbols.

3. The method of claim 1, wherein the first modulated signal and the second modulated signal are simultaneously transmitted over a common frequency channel.

4. The method of claim 3, wherein the common frequency channel has a bandwidth necessary for only one of the first modulated signal and the second modulated signal.

5. A system comprising:
   a processor; and
   a computer-readable storage device storing instructions which, when executed by the processor, cause the processor to perform operations comprising:
      converting each group of successive groups of k incoming bits into a first sequence of symbols and a second sequence of symbols;
      modulating a carrier using the first sequence of symbols to generate a first modulated signal; and
      transmitting the first modulated signal from a first transmitting antenna and a second modulated signal from a second transmitting antenna, wherein the second modulated signal is generated using the second sequence of symbols, and wherein the first transmitting antenna differs from the second transmitting antenna.

6. The system of claim 5, wherein the first sequence of symbols and the second sequence of symbols are different from one another, forming a space-time diversity mapping between the incoming bits and the first sequence of symbols and the second sequence of symbols.

7. The system of claim 5, wherein the first modulated signal and the second modulated signal are simultaneously transmitted over a common frequency channel.

8. The system of claim 7, wherein the common frequency channel has a bandwidth necessary for only one of the first modulated signal and the second modulated signal.

9. A computer-readable storage device having instructions stored which, when executed by a computing device, cause the computing device to perform operations comprising:
   converting each group of successive groups of k incoming bits into a first sequence of symbols and a second sequence of symbols;
   modulating a carrier using the first sequence of symbols to generate a first modulated signal; and
   transmitting the first modulated signal from a first transmitting antenna and a second modulated signal from a second transmitting antenna, wherein the second modulated signal is generated using the second sequence of symbols, and wherein the first transmitting antenna differs from the second transmitting antenna.

10. The computer-readable storage device of claim 9, wherein the first sequence and the second sequence are different from one another, forming a space-time diversity mapping between the incoming bits and the first sequence and the second sequence.

11. The computer-readable storage device of claim 9, wherein the first modulated signal and the second modulated signal are simultaneously transmitted over a common frequency channel.

12. The computer-readable storage device of claim 11, wherein the common frequency channel has a bandwidth necessary for only one of the first modulated signal and the second modulated signal.

* * * * *